US012714878B2

(12) United States Patent
Han et al.

(10) Patent No.: US 12,714,878 B2
(45) Date of Patent: Aug. 25, 2026

(54) METHODS AND SYSTEMS FOR DETERMINING RADIATION FIELD INFORMATION

(71) Applicant: SHANGHAI UNITED IMAGING HEALTHCARE CO., LTD., Shanghai (CN)

(72) Inventors: Mengrong Han, Shanghai (CN); Shuo Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 288 days.

(21) Appl. No.: 18/309,783

(22) Filed: Apr. 29, 2023

(65) Prior Publication Data

US 2023/0347174 A1 Nov. 2, 2023

(30) Foreign Application Priority Data

Apr. 29, 2022 (CN) ......................... 202210465352.9
Apr. 29, 2022 (CN) ......................... 202210466355.4

(51) Int. Cl.
*A61N 5/10* (2006.01)
*G16H 20/40* (2018.01)

(52) U.S. Cl.
CPC ......... *A61N 5/1031* (2013.01); *A61N 5/1039* (2013.01); *G16H 20/40* (2018.01)

(58) Field of Classification Search
CPC ........ A61N 5/10; A61N 5/103; A61N 5/1031; A61N 5/1039; G16H 20/40
See application file for complete search history.

(56) References Cited

U.S. PATENT DOCUMENTS 6,504,899 B2 * 1/2003 Pugachev .............. A61N 5/103 378/65
11,032,469 B2 * 6/2021 Nishii .................... H04N 23/30
(Continued)

FOREIGN PATENT DOCUMENTS

CN 105930636 A 9/2016
CN 109785962 A 5/2019
(Continued)

OTHER PUBLICATIONS

The Second Office Action in Chinese Application No. 202210466355.4 mailed on Nov. 28, 2024, 18 pages.
(Continued)

*Primary Examiner* — Jurie Yun
(74) *Attorney, Agent, or Firm* — METIS IP LLC

(57) ABSTRACT

The embodiments of the present disclosure provide methods and systems for determining radiation field information. The system may include: at least one storage medium including a set of instructions; and at least one processor in communication with the at least one storage medium, wherein when executing the set of instructions, the at least one processor is directed to cause the system to perform operations including: obtaining a candidate beam angle range for an object, the candidate beam angle range including at least one candidate beam angle; determining at least one candidate collimator angle or at least one candidate lock field parameter based on the candidate beam angle range; and determining target radiation field information based on the at least one candidate collimator angle or the at least one candidate lock field parameter.

20 Claims, 15 Drawing Sheets

(56) References Cited

U.S. PATENT DOCUMENTS

| | | | |
|---|---|---|---|
| 2009/0003512 | A1 | 1/2009 | Pouliot et al. |
| 2016/0114192 | A1 | 4/2016 | Lachaine et al. |
| 2019/0336793 | A1 | 11/2019 | Zhou et al. |
| 2020/0054895 | A1 | 2/2020 | Ranganathan |
| 2022/0088410 | A1 | 3/2022 | Hibbard |

FOREIGN PATENT DOCUMENTS

| | | | |
|---|---|---|---|
| CN | 110211664 | A | 9/2019 |
| CN | 110292723 | A | 10/2019 |
| CN | 110465004 | A | 11/2019 |
| CN | 110582328 | A | 12/2019 |
| CN | 111402305 | A | 7/2020 |
| CN | 111888667 | A | 11/2020 |
| CN | 112512632 | B | 2/2023 |

OTHER PUBLICATIONS

First Office Action in Chinese Application No. 202210465352.9 mailed on May 29, 2024, 19 pages.
Shao, Zhiming et al., Oncology, 2019, 36 pages.
James D. Cox et al., Image-Guided Radiotherapy of Lung Cancer, 2007, 6 pages.
Bortfeld Thomas et al., Image-Guided IMRT, 2007, 10 pages.

* cited by examiner

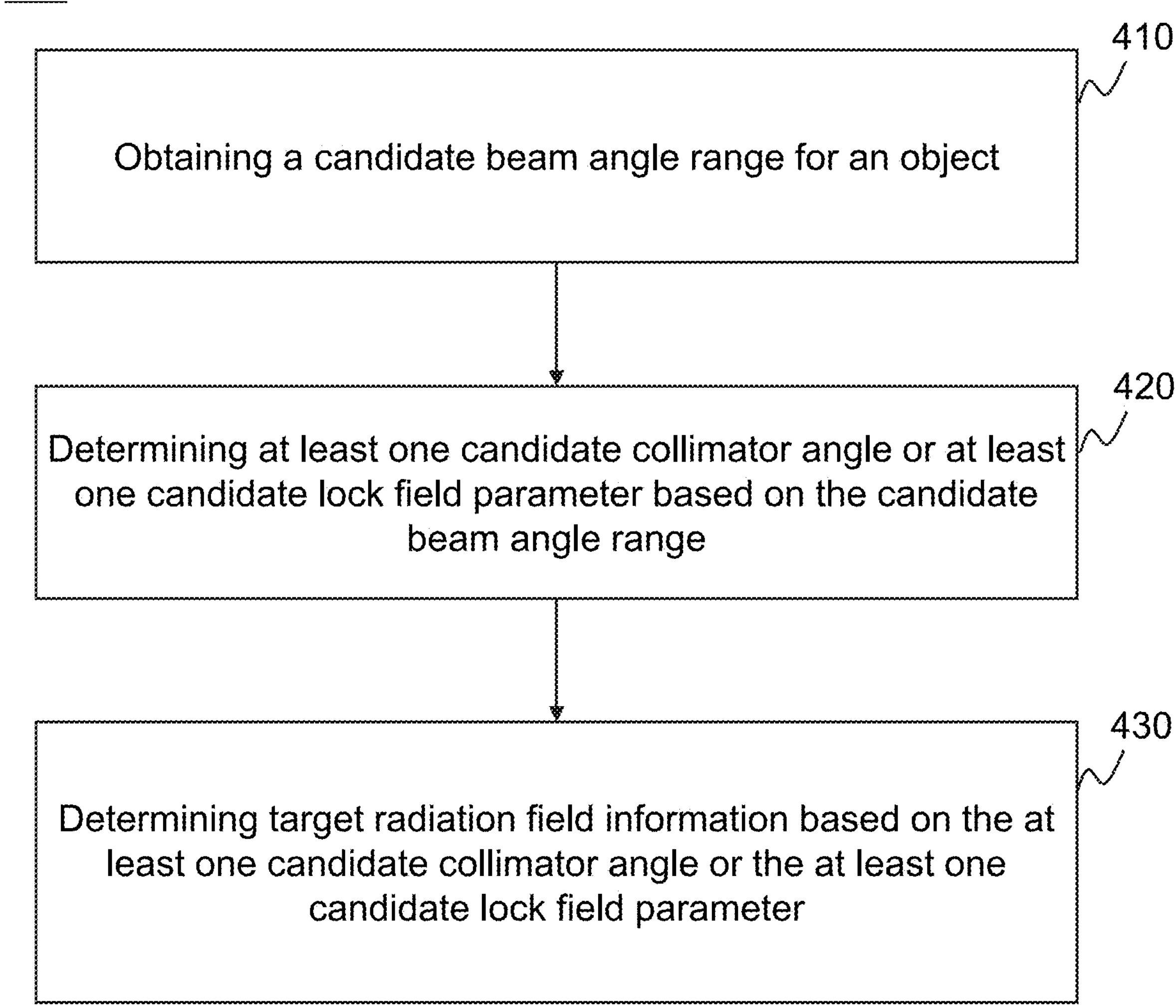
FIG. 4

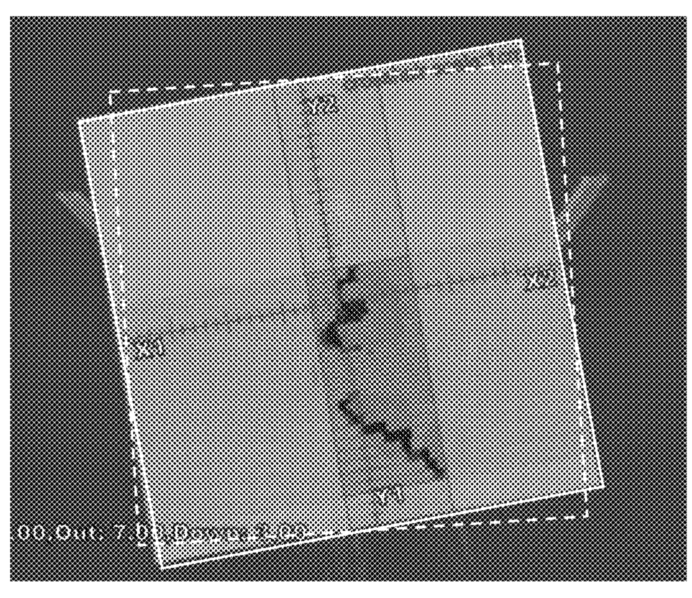
(a)
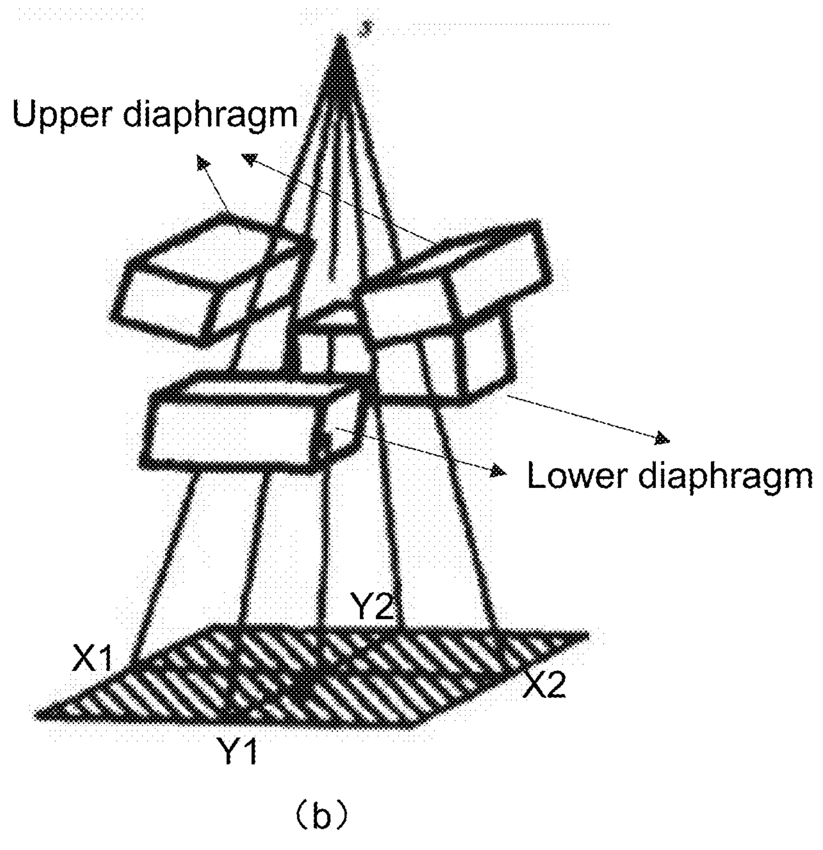
(b)
FIG. 5

Figure 9:
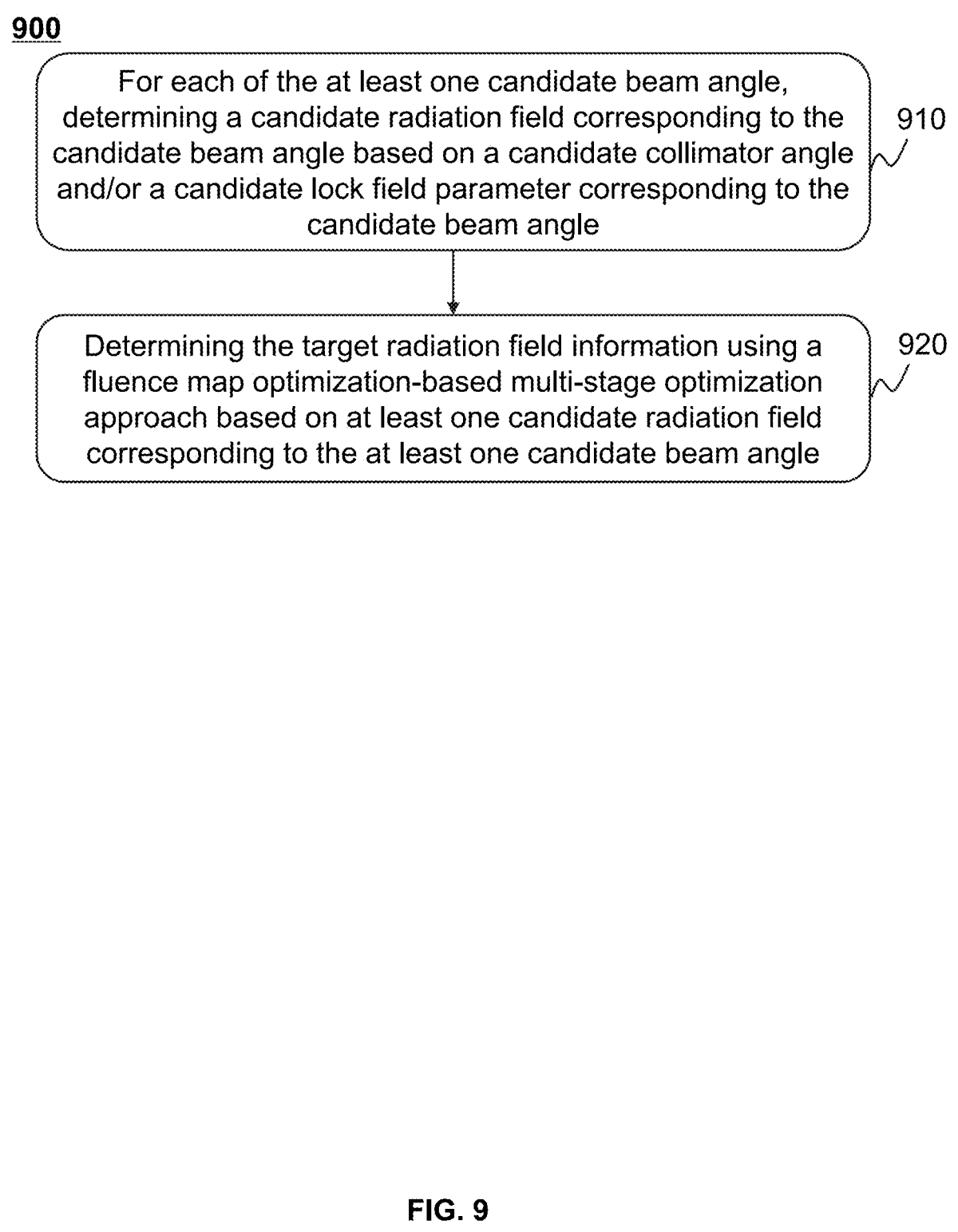

900

For each of the at least one candidate beam angle, determining a candidate radiation field corresponding to the candidate beam angle based on a candidate collimator angle and/or a candidate lock field parameter corresponding to the candidate beam angle

910

Determining the target radiation field information using a fluence map optimization-based multi-stage optimization approach based on at least one candidate radiation field corresponding to the at least one candidate beam angle

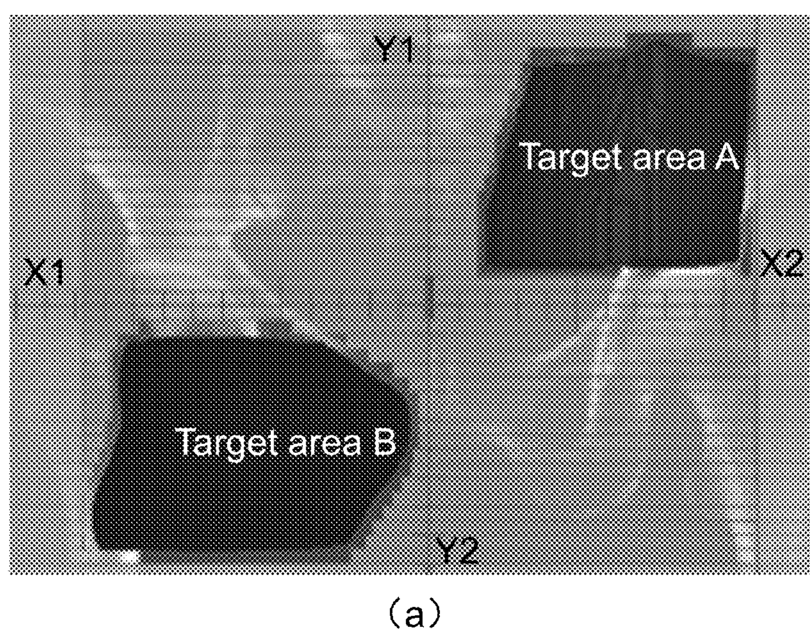
(a)
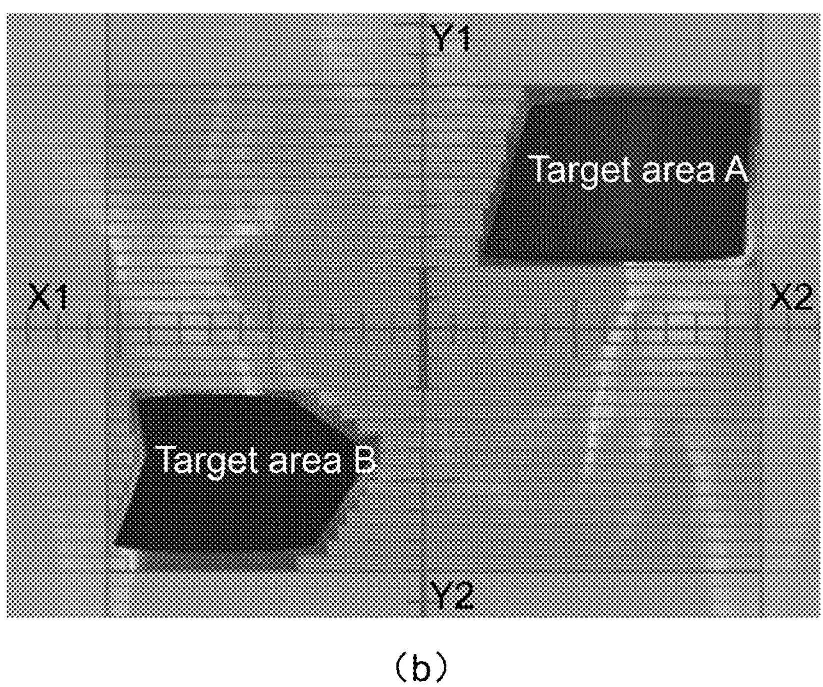
(b)
FIG. 13

METHODS AND SYSTEMS FOR DETERMINING RADIATION FIELD INFORMATION

CROSS-REFERENCE TO RELATED APPLICATIONS

This application claims priority to Chinese Patent Application No. 202210466355.4, filed on Apr. 29, 2022, and Chinese Patent Application No. 202210465352.9, filed on Apr. 29, 2022, the entire contents of which are hereby incorporated by reference.

TECHNICAL FIELD

The present disclosure generally relates to the field of medical technology, and in particular, to methods and systems for determining radiation field information.

BACKGROUND

Radiation therapy is a medical manner for treating a disease such as a malignant tumor. Before radiation therapy, it is often necessary to determine a treatment plan used to achieve a therapeutic goal. The treatment plan may include radiation field information such as a beam angle, a radiation intensity level, a collimator angle, a lock field parameter, etc. It is important to accurately and efficiently determine proper radiation field information to achieve the therapeutic goal. Therefore, it is desirable to provide methods and systems for automatically determining radiation field information to improve the quality and production efficiency of the treatment plan.

SUMMARY

In one aspect of the present disclosure, a system for determining radiation field information is provided. The system may include: at least one storage medium including a set of instructions; and at least one processor in communication with the at least one storage medium, wherein when executing the set of instructions, the at least one processor is directed to cause the system to perform operations including: obtaining a candidate beam angle range for an object; determining at least one candidate collimator angle or at least one candidate lock field parameter based on the candidate beam angle range; and determining target radiation field information based on the at least one candidate collimator angle or the at least one candidate lock field parameter.

In some embodiments, the obtaining a candidate beam angle range for an object may include: determining, based on case information of the object, a target historical case corresponding to the case information, the case information including a tumor type or reference information related to a region of interest (ROI); and determining the candidate beam angle range for the object based on the target historical case.

In some embodiments, the candidate beam angle range may include at least one candidate beam angle, and the determining at least one candidate collimator angle or at least one candidate lock field parameter based on the candidate beam angle range may include: for each of the at least one candidate beam angle, determining the collimator angle corresponding to the candidate beam angle through geometry optimization; or determining the lock field parameter corresponding to the candidate beam angle using a lock field parameter determination model.

In some embodiments, the candidate beam angle range may include at least one candidate beam angle, and the determining at least one candidate collimator angle or at least one candidate lock field parameter based on the candidate beam angle range may include: for each of the at least one candidate beam angle, determining the collimator angle and the lock field parameter corresponding to the candidate beam angle using a radiation field information determination model.

In some embodiments, the candidate beam angle range may include at least one candidate beam angle, and the determining target radiation field information based on the at least one candidate collimator angle or the at least one candidate lock field parameter may include: for each of the at least one candidate beam angle, determining a candidate radiation field corresponding to the candidate beam angle based on the collimator angle or the lock field parameter corresponding to the candidate beam angle; and determining the target radiation field information using a fluence map optimization-based multi-stage optimization approach based on at least one candidate radiation field corresponding to the at least one candidate beam angle.

In some embodiments, the operations may further include: obtaining a first image of the object corresponding to the target radiation field information; obtaining a second image of the object; determining relevant information of the second image and the first image; and determining adjusted radiation field information corresponding to the second image based on the relevant information and the target radiation field information.

In some embodiments, the first image or the second image may include at least one of target area information or organ at risk (OAR) information of the object.

In some embodiments, the relevant information may include at least one of a registration parameter or a target area projection similarity; and the registration parameter may include a rigid registration parameter or a non-rigid registration parameter determined based on anatomical structures in the first image and the second image.

In some embodiments, the determining adjusted radiation field information corresponding to the second image based on the relevant information and the target radiation field information may include: determining an initial beam angle corresponding to the second image based on a rigid registration parameter of the second image and the first image and a target beam angle of the target radiation field information; and determining an adjusted beam angle corresponding to the second image by adjusting the initial beam angle based on a target area projection similarity of the second image and the first image.

In some embodiments, the determining an adjusted beam angle corresponding to the second image by adjusting the initial beam angle based on a target area projection similarity of the second image and the first image may include: determining an initial angle adjustment range based on the initial beam angle corresponding to the second image; determining a plurality of reference beam angles based on the initial angle adjustment range; determining a similarity between a target area projection corresponding to each reference beam angle and a target area projection of the first image; updating the initial angle adjustment range based on a plurality of similarities of target area projection corresponding to the plurality of reference beam angles respectively; and determining the adjusted beam angle based on the updated angle adjustment range.

In some embodiments, the determining adjusted radiation field information corresponding to the second image based on the relevant information and the target radiation field information may include: determining an adjusted collimator angle corresponding to the second image based on a rigid registration parameter of the second image and the first image and a target collimator angle of the target radiation field information.

In some embodiments, the determining adjusted radiation field information corresponding to the second image based on the relevant information and the target radiation field information may include: determining an adjusted lock field parameter corresponding to the second image based on a non-rigid registration parameter of the second image and the first image and a target lock field parameter of the target radiation field information.

In some embodiments, after obtaining the second image of the object, the operations may further include: determining a similarity between the second image and the first image; and providing a notification in response to a determination that the similarity is smaller than a preset threshold.

In some embodiments, the operations may further include: updating a treatment plan of the object based on the adjusted radiation field information, wherein the treatment plan is determined based on the target radiation field information.

In some embodiments, the updating a treatment plan of the object based on the adjusted radiation field information may include: obtaining first target area information or first OAR information corresponding to the first image; obtaining second target area information and second OAR information corresponding to the second image; determining at least one adjusted parameter corresponding to at least one parameter of the treatment plan using an updating model based on the target radiation field information, the adjusted radiation field information, the first target area information, the first OAR information, the second target area information, and the second OAR information; and updating the treatment plan of the object based on the at least one adjusted parameter corresponding to the at least one parameter.

In some embodiments, the operations may further include: obtaining a first image of the object corresponding to the target radiation field information; obtaining a second image of the object; and determining, based on the first image and the second image, adjusted radiation field information corresponding to the second image using a radiation field information adjustment model.

In another aspect of the present disclosure, a method for determining radiation field information is provided. The method may include: obtaining a candidate beam angle range for an object; determining at least one candidate collimator angle or at least one candidate lock field parameter based on the candidate beam angle range; and determining target radiation field information based on the at least one candidate collimator angle or the at least one candidate lock field parameter.

In some embodiments, the candidate beam angle range may include at least one candidate beam angle, and the determining target radiation field information based on the at least one candidate collimator angle or the at least one candidate lock field parameter may include: for each of the at least one candidate beam angle, determining a candidate radiation field corresponding to the candidate beam angle based on the collimator angle or the lock field parameter corresponding to the candidate beam angle; and determining the target radiation field information using a fluence map optimization-based multi-stage optimization approach based on the at least one candidate radiation field corresponding to the at least one candidate beam angle.

In some embodiments, the method may further include: obtaining a first image of the object corresponding to the target radiation field information; obtaining a second image of the object; determining relevant information of the second image and the first image; and determining adjusted radiation field information corresponding to the second image based on the relevant information and the target radiation field information.

In another aspect of the present disclosure, another system for determining radiation field information is provided. The system may include: at least one storage medium including a set of instructions; and at least one processor in communication with the at least one storage medium, wherein when executing the set of instructions, the at least one processor is directed to cause the system to perform operations including: obtaining a first image of an object; obtaining a second image of the object; determining relevant information of the first image and the second image; and determining second radiation field information corresponding to the second image based on the relevant information and first radiation field information corresponding to the first image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 4 is a flowchart illustrating an exemplary process for determining radiation field information according to some embodiments of the present disclosure;

FIG. 5 is a schematic diagram illustrating exemplary radiation field information according to some embodiments of the present disclosure;

FIG. 9 is a flowchart illustrating an exemplary process for determining target radiation field information according to some embodiments of the present disclosure;

FIG. 13 is a schematic diagram illustrating an exemplary target area projection according to some embodiments of the present disclosure;

DETAILED DESCRIPTION

Figure 1:
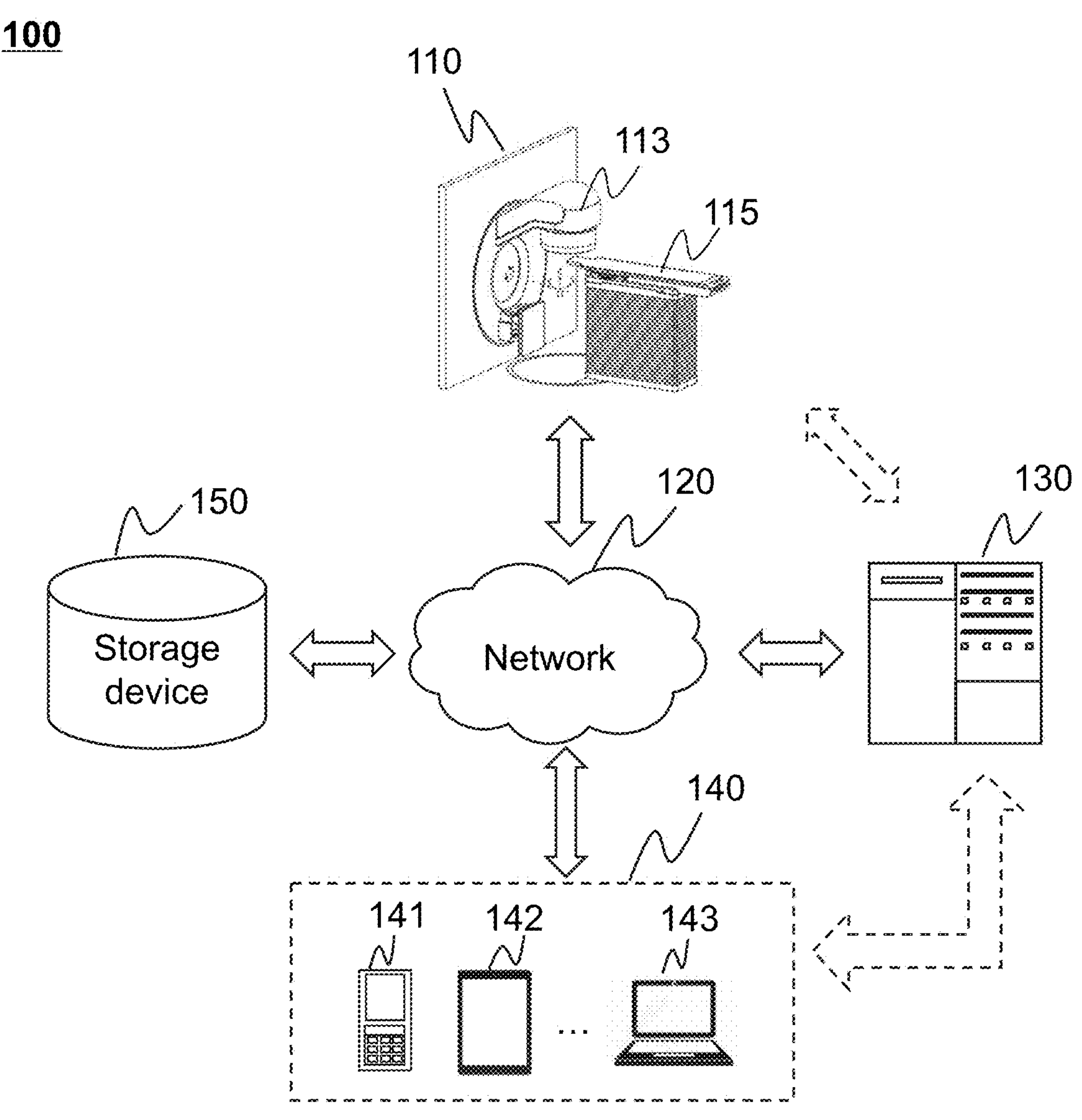
FIG. 1 is a schematic diagram illustrating an exemplary medical system according to some embodiments of the present disclosure.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

The terms "comprise," "comprises," "comprising," "include," "includes," "including," "have," "has," "having," and any variations thereof referred to in the present disclosure are intended to cover non-exclusive inclusions. For example, a process, a method, a system, a product, or a device including a series of operations or modules (units) is not limited to the operations or units listed, but may also include operations or units that are not listed, or may also include other operations or units inherent to the process, the method, the product or the device. The "a plurality of" referred to in the present disclosure refers to greater than or equal to two. "And/or" describes an association relationship of associated objects, indicating that three kinds of relationships may exist, for example, "A and/or B" may indicate that A exists alone, A and B exist simultaneously, and B exists alone. The terms "first," "second," "third," and "fourth," etc. referred to in the present disclosure are only to distinguish similar objects, and do not represent a specific order for the objects.

The flowcharts used in the present disclosure illustrate operations that systems implement according to some embodiments in the present disclosure. Relevant descriptions is provided to assist in a better understanding of medical imaging methods and/or systems. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

In the present disclosure, the terms "radiation therapy," "radiotherapy," and "treatment" may be used interchangeably to refer to treating a patient. The terms "target object," "patient," "treatment area," and "tumor" may be used interchangeably to refer to a treatment object and/or a treatment area. The terms "area," "target area", "position," and "treatment area" may refer interchangeably to a position of a treatment area shown in an image or an actual position of the treatment area within or on a body of the patient. The term "image" may refer to a two-dimensional (2D) image, a three-dimensional (3D) image, or a four-dimensional (4D) image.

During preparation of a treatment plan of the radiation therapy (e.g., Intensity-Modulated Radiation Therapy (IMRT)), a physicist (e.g., a doctor) may usually set a beam angle and a lock field parameter based on a positional relationship between the target area and an organ based on his/her own experience. However, in the case of a relatively complicated case (e.g., a breast case) and/or a new physicist preparing the treatment plan, a manner based on manual experience may easily lead to an unreasonable beam angle and/or an unreasonable lock field parameter, which may in turn affect the quality of the treatment plan. Therefore, in order to minimize the impact of the beam angle and the lock field parameter on the quality of the treatment plan, a trial and error method may be used, which may increase the complexity of the preparation of the treatment plan to a certain extent. In some cases, the beam angle may be optimized automatically. However, for a complicated case (e.g., a case of radical mastectomy with a collarbone), merely automatic optimization of the beam angle (i.e., optimization without the lock field parameter) not only may not protect a lung, a heart, etc., but also may require a user to optimize the treatment plan by making changes on the basis of automatic field deployment, which may affect the realization of a one-stop workflow.

In addition, in the online adaptive process of radiotherapy, the radiation field setting of the adaptive plan may usually continue to use the radiation field information (e.g., the beam angle, a collimator angle, the lock field parameter (e.g., locking position of a jaw)) of an original plan, regardless of the effect of deformation and/or rotation of the target area on the radiation field setting. If the radiation field information corresponding to a current image is manually modified based on a change in an anatomical structure in a planned image (e.g., a first image) and the current image (e.g., a second image), which may not only prolong a time of adaptive radiotherapy workflow, but also be difficult to avoid the risk of a human error in a high-pressure environment.

The embodiments of present disclosure provide methods and systems for determining radiation field information. The systems may determine a candidate beam angle range of an object; for each candidate beam angle in the candidate beam angle range, the systems may determine a candidate collimator angle and a candidate lock field parameter corresponding to the candidate beam angle; then the systems may determine target radiation field information based on at least one candidate collimator angle and at least one candidate lock field parameter corresponding to the at least one candidate beam angle. During the process, big data involving field deployment information (e.g., field deployment information corresponding to historical cases), a geometric relationship between the target area and the organ, and automatic determination of the lock field parameter and/or the collimator angle by a machine learning model, which can not only reduce the impact of the radiation field information on the effect of the treatment plan and improve the quality of the treatment plan, but also shorten the time for preparing the treatment plan and integrate the preparation of the treatment plan into the online automatic planning process, thereby improving the efficiency of preparing the treatment plan.

Further, according to the embodiments of present disclosure, the systems may determine adjusted radiation field information corresponding to a second image (which is collected after the first image) based on the target radiation field information and relevant information between a first image corresponding to the target radiation field information and the second image, which may not only take into account the effect of the deformation and/or rotation of the target area on the radiation field setting, but also avoid the risk of error caused by manually setting the radiation field parameter and prolong the time of radiotherapy workflow, thereby improving the convenience of operation and the efficiency of radiation field information adjustment.

FIG. 1 is a schematic diagram illustrating an exemplary medical system according to some embodiments of the present disclosure. As shown in FIG. 1, in some embodiments, the medical system 100 may include a medical device 110, a network 120, a processing device 130, a terminal device 140, and a storage device 150. The medical system 100 may be connected in various manners. Merely by way of example, the medical device 110 may be connected to the terminal device 140 through the network 120. As another example, the medical device 110 may be connected to the processing device 130 through the network 120 or directly. As a further example, the processing device 130 may be connected to the terminal device 140 through the network 120 or directly.

The medical device 110 may obtain an image of an object and/or execute a treatment plan on the object. For example, the medical device 110 may perform radiation therapy on a lesion area (also referred to as a target area) such as a target tumor, etc. of the object. As another example, the medical device 110 may obtain a current image by imaging the object and perform the radiation therapy based on the current image. In some embodiments, the object may include a biological object and/or a non-biological object. The biological object may be a human being, an animal, a plant, or a specific portion, organ, and/or tissue thereof. In some embodiments, the object may include a specific part of the body, such as a head, a chest, an abdomen, or the like, or any combination thereof. In some embodiments, the object may include a specific organ, such as a heart, a breast, an esophagus, a trachea, bronchus, a stomach, a gallbladder, a small intestine, a colon, a bladder, a ureter, a uterine, a tubal, etc. In some embodiments, the object may include a patient or other medical experimental objects (e.g., other animals such as a mouse for experiment). In some embodiments, the object may include a region of interest (ROI), for example, a tumor, a nodule, an organ at risk (OAR), etc.

In some embodiments, the medical device 110 may include one or more medical devices. In some embodiments, one of the one or more medical devices may be used for both imaging and treatment. In some embodiments, the imaging and treatment may be performed by different medical devices.

In some embodiments, the medical device 110 may include a radiotherapy device, which may be used to perform the radiation therapy on the target area, such as the tumor, etc. of the object. In some embodiments, the radiotherapy device may include a single-modal device such as an X-ray therapy device, a Co-60 teletherapy device, a medical electron accelerator, etc. In some embodiments, the radiotherapy device may include a multimodal (e.g., dual-modal) device. In some embodiments, the multimodal device may obtain a medical image related to at least one part of the object and perform the radiation therapy on the at least one part of the object. For example, the radiotherapy device may include an image guided radiation therapy (IGRT) device (e.g., a computed tomography (CT) guided radiation therapy device and a magnetic resonance imaging (MRI) guided radiation therapy device). In some embodiments, the radiotherapy device may also include an IMRT device. The IMRT device may make a radiation dose more accurate by adjusting (or controlling) intensity of radiation according to a shape of the target area.

In some embodiments, the medical device 110 may include a fixed part and a rotating part. The rotating part may be mounted on the fixed part and the rotating part may rotate around a central axis, so as to perform the radiation therapy on a patient at different angles. One side of the rotating part may include or be mounted with a treatment head (e.g., a treatment head 113). The treatment head may generate a high-level beam to perform the radiation therapy on the object on a medical couch (e.g., a medical couch 115). The beam may include an electron, a photon, or any other type of radiation. In some embodiments, the medical device 110 may include a homologous dual-beam radiotherapy device. The treatment head may generate a low-level X-ray for imaging the patient and perform image guided radiation therapy on the patient using an obtained patient image. When the imaging is performed by the low-level X-ray, the treatment head may emit a cone-beam of X-ray, an imaging device (e.g., an electronic portal imaging devices (EPID)) on the other side of the rotating part may receive the X-ray passing through the patient, and a projection image may be formed at the angle. When the treatment head is irradiated at different angles, projection images of a plurality of angles may be formed.

In some embodiments, the treatment head may include a collimator for beam shaping. The collimator may be rotated around a rotation axis to enable the treatment head to form various desired beam shapes (e.g., shapes close to the target area). In some embodiments, the collimator may include a primary collimator and a secondary collimator.

The primary collimator refers to a fixed collimator with a conical hole. On the one hand, the primary collimator may be used to determine a maximum radiation field range that the accelerator can provide. On the other hand, the primary collimator (e.g., a multi-leaf collimator (MLC)) may be used to block primary radiation generated by a radiation source outside the maximum radiation field range. In some embodiments, at least one part of the beam may be blocked by the primary collimator. The MLC (also referred to as a multi-leaf grating or a multi-leaf diaphragm) may be composed of two groups of closely arranged leaves. Each leaf may be in the shape of a long strip and driven by a small motor, so that an area (e.g., a radiation field) for the radiation source to irradiate may be formed through the plurality of closely arranged leaves. An area blocked by the leaves of the MLC may not be irradiated, so that a required radiation dose may be accurately projected to the treatment target area of the patient and protection of surrounding normal tissue may be maximized.

The secondary collimator refers to a device for secondary collimation of the beam. For example, the secondary collimator may be composed of upper and lower pairs of rectangular collimators (also referred to as upper and lower diaphragms or jaws) that can be opened and closed. Through the opening and closing of the upper and lower pairs of rectangular collimators, a square or rectangular radiation field may be formed.

In some embodiments, the medical device 110 may include an imaging device. For example, the imaging device may include an X-ray device, a computed tomography imaging device (CT), a three-dimensional (3D) CT, a four-dimensional (4D) CT, an ultrasound imaging component, a fluoroscopy imaging component, a magnetic resonance imaging (MRI) device, a single photon emission computed tomography (SPECT) device, a positron emission tomography (PET) device, or the like, or any combination thereof. The imaging device disclosed above is merely for the purpose of illustration and is not intended to limit the scope of the present disclosure.

The network 120 may include any suitable network that can facilitate the exchange of information and/or data for the medical system 100. In some embodiments, one or more components (e.g., the medical device 110, the processing device 130, the terminal device 140, the storage device 150) of the medical system 100 may communicate information and/or data with one or more other components of the medical system 100 via the network 120. For example, the processing device 130 may obtain a first image of the object and/or a second image of the object from the medical device 110 through the network 120.

In some embodiments, the network 120 may include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network (VPN), a satellite network, a telephone network, routers, hubs, server computers, and/or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The processing device 130 may process data and/or information obtained from the medical device 110, the terminal device 140, and/or the storage device 150. For example, the processing device 130 may obtain a candidate beam angle range for an object, the candidate beam angle range including at least one candidate beam angle. For each of the at least one candidate beam angle, the processing device 130 may determine a candidate collimator angle and a candidate lock field parameter based on the candidate beam angle, and determine target radiation field information based on at least one candidate collimator angle and at least one candidate lock field parameter corresponding to the at least one candidate beam angle. As another example, the processing device 130 may process a first image of the object corresponding to the target radiation field information and a second image of the object generated by the medical device 110 to determine adjusted radiation field information corresponding to the second image.

In some embodiments, the processing device 130 may be a single server or a server group. The server group may be centralized or distributed. In some embodiments, the processing device 130 may be local or remote. For example, the processing device 130 may access information and/or data from the medical device 110, the terminal device 140, and/or the storage device 150 via the network 120. As another example, the processing device 130 may be directly connected to the medical device 110, the terminal device 140, and/or the storage device 150 to access information and/or data. In some embodiments, the processing device 130 may be implemented on a cloud platform. For example, the cloud platform may include a private cloud, a public cloud, a hybrid cloud, a community cloud, a distributed cloud, an inter-cloud, a multi-cloud, or the like, or any combination thereof.

The terminal device 140 may communicate and/or be connected with the medical device 110, the processing device 130, and/or the storage device 150. For example, the terminal device 140 may determine a dose determination result during the radiotherapy from the processing device 130. As another example, the terminal device 140 may obtain an image (e.g., the first image of the object) acquired by the medical device 110, and transmit the image to the processing device 130 for processing. In some embodiments, the terminal device 140 may include a mobile device 141, a tablet computer 142, a laptop computer 143, a desktop computer, or any combination thereof. In some embodiments, the terminal device 140 may include an input device, an output device, etc. The input device may include a keyboard input, a touch screen (e.g., with tactile or tactile feedback) input, a voice input, an eye-tracking input, a brain monitoring system input, or any other similar input mechanism. The output device may include a display, a speaker, a printer, or any combination thereof. In some embodiments, the terminal device 140 may be part of the processing device 130. In some embodiments, the terminal device 140 and the processing device 130 may be integrated as a control device of the medical device 110, such as an operation console. In some embodiments, the terminal device 140 may be omitted.

The storage device 150 may store data, instructions and/or any other information. In some embodiments, the storage device 150 may store data obtained from the medical device 110, the processing device 130, and/or the terminal device 140. For example, the storage device 150 may store the first image, the second image, the candidate beam angle range, the candidate collimator angle, and/or the candidate lock field parameter, obtained from the medical device 110. In some embodiments, the storage device 150 may store data and/or instructions that the processing device 130 may execute or use to perform exemplary methods described in the present disclosure. In some embodiments, the storage device 150 may include a mass storage, a removable storage, a volatile read-and-write memory, a read-only memory (ROM), or the like, or any combination thereof.

In some embodiments, the storage device 150 may be connected to the network 120 to communication with one or more components (e.g., the medical device 110, the processing device 130, the terminal device 140) of the medical system 100. One or more components of the medical system 100 may assess the data or instructions stored in the storage device 150 via the network 120. In some embodiments, the storage device 150 may be a part of the processing device 130, or may be independent, and directly or indirectly connected to the processing device 130.

It should be noted that the above description of the medical system 100 is merely provided for the purpose of illustration, and is not intended to limit the scope of the present disclosure. For persons having ordinary skills in the art, a plurality of variations and modifications may be made under the teachings of the present disclosure. However, those variations and modifications do not depart from the scope of the present disclosure. For example, the medical device 110, the processing device 130 and the terminal device 140 may share the storage device 150, or may have their own storage devices.

Figure 2:
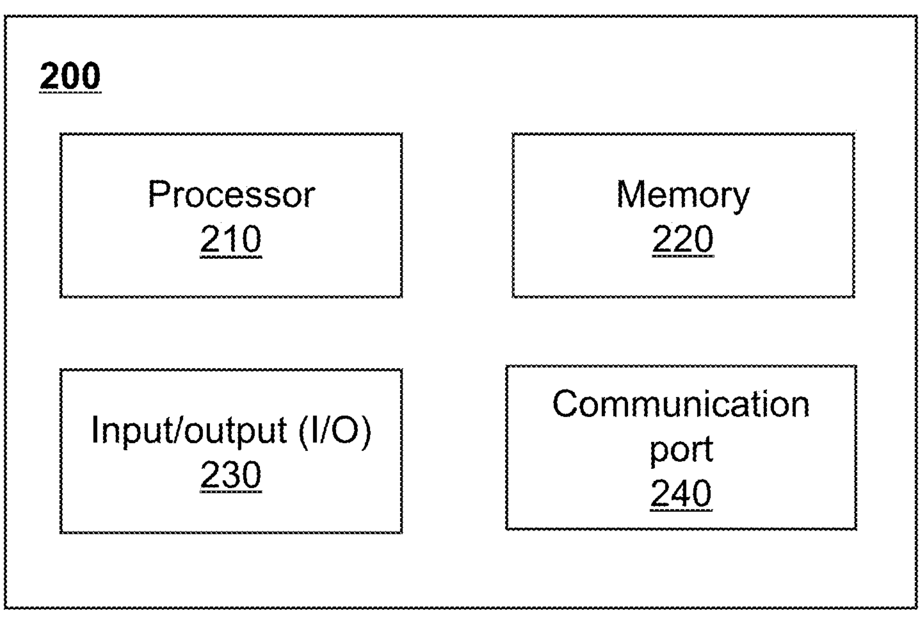
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure.

As shown in FIG. 2, in some embodiments, the computing device 200 may include a processor 210, a memory 220, an input/output (I/O) 230, and a communication port 240.

The processor 210 may execute computer instructions (e.g., program code) and perform functions of the processing device 130 according to the method(s) described herein. The computer instructions may include, for example, routines, programs, objects, components, data structures, procedures, modules, and functions, which perform particular functions described herein. For example, the processor 210 may process data of the medical device 110, the terminal device 140, the storage device 150, and/or any other component in the medical system 100. In some embodiments, the processor 210 may include at least one hardware processor, such as a microcontroller, a microprocessor, a reduced instruction set computer (RISC), an application specific integrated circuit (ASIC), an application specific instruction set processor (ASIP), a central processing unit (CPU), a graphics processing unit (GPU), a physical processing unit (PPU), microcontroller unit, a digital signal processor (DSP), a field programmable gate array (FPGA), a high-order RISC Machine (ARM), a programmable logic device (PLD), any circuit or processor or similar capable of performing at least one function, or any combination thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operations A and B, it should be understood that operation A and operation B may also be performed by two or more different processors jointly or separately in the computing device 200 (e.g., a first processor executes operation A and a second processor executes operation B, or the first and second processors jointly execute operations A and B).

The memory 220 may store data/information obtained from the medical device 110, the terminal device 140, the storage device 150, and/or any other component in the medical system 100. In some embodiments, the memory 220 may include a mass storage, a removable storage, a volatile read-write memory, a read-only memory (ROM), or any combination thereof. In some embodiments, the memory 220 may store at least one program and/or instruction for executing the exemplary manner described in the present disclosure.

The input/output (I/O) 230 may be used to input and/or output signal, data, information, etc. In some embodiments, the input/output (I/O) 230 may enable the user to interact with processing device 130. In some embodiments, the input/output (I/O) 230 may include an input device and an output device. An exemplary input device may include a keyboard, a mouse, a touch screen, a microphone, or any combination thereof. The exemplary output device may include a display device, a speaker, a printer, a projector, or any combination thereof. An exemplary display device may include a liquid crystal display (LCD), a light emitting diode (LED)-based display, a flat panel display, a curved surface display, a television device, a cathode ray tube, or any combination thereof.

The communication port 240 may be connected with a network (e.g., the network 120) to facilitate data communication. The communication port 240 may establish a connection between the processing device 130 and the medical device 110, the terminal device 140, and/or the storage device 150. The connection may include a wired connection and a wireless connection. The wired connection may include, for example, cable, optical cable, telephone line, or any combination thereof. The wireless connection may include, for example, Bluetooth link, Wi-Fi™ link, WiMax™ link, WLAN link, ZigBee link, mobile network link (e.g., 3G, 4G, 5G), or any combination thereof. In some embodiments, the communication port 240 may be and/or include a standardized communication port, such as RS232, RS485, etc. In some embodiments, the communication port 240 may be a specially designed communication port. For example, the communication port 240 may be designed according to a digital imaging and medical communication (DICOM) protocol.

Figure 3:
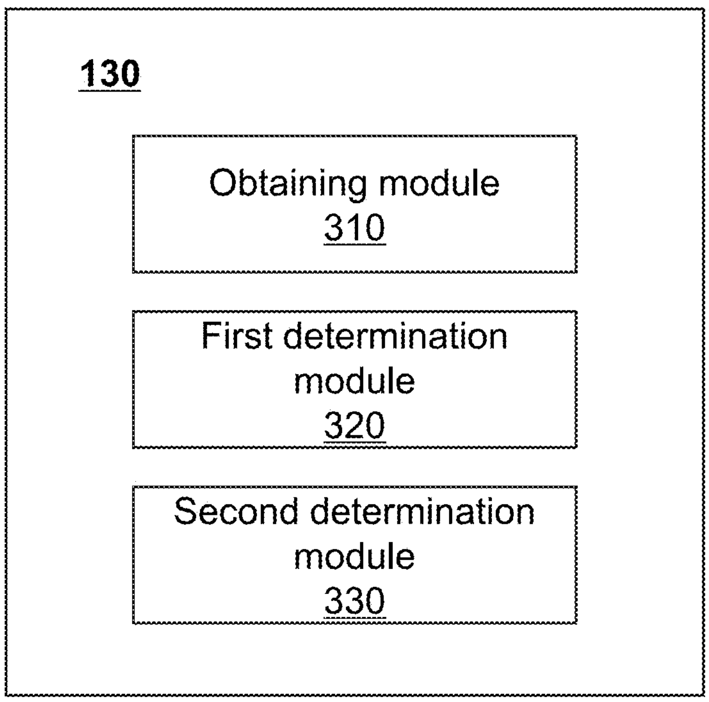
FIG. 3 is a block diagram illustrating an exemplary processing device according to some embodiments of the present disclosure.

FIG. 3 is a block diagram illustrating an exemplary processing device according to some embodiments of the present disclosure.

As shown in FIG. 3, in some embodiments, the processing device 130 may include an obtaining module 310, a first determination module 320, and a second determination module 330.

The obtaining module 310 may be configured to obtain a candidate beam angle range for an object, the candidate beam angle range including at least one candidate beam angle. The first determination module 320 may be configured to, for each of the at least one candidate beam angle, determine a candidate collimator angle and a candidate lock field parameter based on the candidate beam angle. The second determination module 330 may be configured to determine target radiation field information based on at least one candidate collimator angle and at least one candidate lock field parameter corresponding to the at least one candidate beam angle. More descriptions regarding the obtaining module 310, the first determination module 320, and the second determination module 330 may be found in FIG. 4 and the related descriptions thereof, which will not be repeated herein.

In some embodiments, the processing device 130 may further include an adjusted radiation field information determination module, a treatment plan determination module, and a prompting module (not shown).

The adjusted radiation field information determination module may be configured to determine adjusted radiation field information corresponding to a second image based on relevant information of the second image and a first image and the target radiation field information.

The treatment plan determination module may be configured to determine a treatment plan of an object based on the target radiation field information. In some embodiments, the treatment plan determination module may also be configured to update the treatment plan of the object based on the adjusted radiation field information.

The prompting module may be configured to provide a notification in response to a determination that a similarity between the second image and the first image is smaller than a preset threshold.

It should be understood that the systems and modules shown in FIG. 3 may be implemented in various ways. For example, in some embodiments, at least one of the obtaining module 310, the first determination module 320 and the second determination module 330 may be implemented entirely by hardware, software, or by combining software and hardware implementation. For example, the obtaining module 310, the first determination module 320 and the second determination module 330 may share a processor and a non-transitory storage medium or have their own processors and non-transitory storage mediums. The non-transitory storage medium may store a computer program. When the processor executes the computer program, a corresponding function may be implemented.

FIG. 4 is a flowchart illustrating an exemplary process for determining radiation field information according to some embodiments of the present disclosure. In some embodiments, process 400 may be executed by the medical system 100. For example, the process 400 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 400. The operations of the illustrated process presented below are intended to be illustrative. In some embodiments, the process 400 may be accomplished with one or more additional operations not described and/or without one or more of the operations discussed. Additionally, the order of the operations of process 400 illustrated in FIG. 4 and described below is not intended to be limiting.

In 410, the processing device 130 (e.g., the obtaining module 310, the processor 210) may obtain a candidate beam angle range for an object.

The candidate beam angle range refers to an angle candidate pool used to determine a beam angle corresponding to a treatment plan. In some embodiments, the candidate angle range may include any interval within [0°, 360° ], for example, [0°, 90° ], [0°, 180° ], [5°, 10° ], [0°, 45° ], etc.

In some embodiments, the processing device 130 may determine, based on case information of the object, a target historical case corresponding to the case information, and determine the candidate beam angle range for the object based on the target historical case.

In some embodiments, the case information may include a tumor type and/or reference information related to a region of interest (ROI).

In some embodiments, the tumor type may include a tissue source of the tumor (e.g., an epithelial tumor, a mesenchymal tumor, a neurogenic tumor, a lymphogenic tumor), a nature of the tumor (e.g., a benign tumor, a borderline tumor, a malignant tumor), a tumor growth pattern (e.g., a carcinoma in situ, an infiltrating carcinoma, a metastatic carcinoma), an extent of tumor invasion (e.g., an early cancer, an intermediate cancer, an advanced cancer), a degree of malignancy of the tumor (e.g., a low-grade malignant tumor, a moderately malignant tumor, a high-grade malignant tumor), an anatomical site corresponding to the tumor (e.g., a breast tumor, a lung tumor, an uterine tumor, a gastric tumor), or the like, or any combination thereof.

In some embodiments, the ROI may include a target area and/or an organ at risk (OAR). The target area refers to an area where the object needs radiation therapy, for example, a tumor area. The OAR refers to an important viscus or organ involved in a radiation field during the radiation therapy. Due to high radio sensitivity (low tolerated dose) of the organs, radiation damage may seriously affect life of a patient or quality of life, accordingly, the design and implementation of an irradiation plan (i.e., the treatment plan) may be directly affected by the OAR. In some embodiments, the processing device 130 may mark the target area and/or the OAR (e.g., circle an area where the target area and/or the OAR is located in a target image) and determine the ROI. In some embodiments, the reference information related to the ROI may include a position of the target area and/or the OAR, a size of the target area and/or the OAR, a relative positional relationship between the target area and the OAR, or the like, or any combination thereof.

In some embodiments, the processing device 130 may determine the target historical case corresponding to the case information based on a correlation between the case information of the object and historical case information. For example, the processing device 130 may retrieve a historical case similar to or the same as the case information of the object from a database (e.g., the storage device 150), and determine the candidate beam angle range of the object based on radiation field information such as a beam angle, a collimator angle, a lock field parameter, etc. corresponding to the similar or the same historical case, More descriptions regarding the determining the candidate beam angle range may be found in FIG. 6 and the related descriptions thereof, which will not be repeated herein.

In some embodiments, the candidate beam angle range may include at least one candidate beam angle.

In some embodiments, the processing device 130 may adjust the candidate beam angle range based on a user instruction. For example, the processing device 130 may adjust the candidate beam angle range of the object based on an adjustment parameter related to the candidate beam angle range input by the user through the terminal device 140. In some embodiments, the adjustment parameter may include, but is not limited to, a maximum/minimum interval, an angle interval, a count of angles, or the like, or any combination thereof. The maximum/minimum interval refers to a range interval that the candidate beam angle range needs to satisfy (e.g., in a range of [0°, 180° ]). The angle interval refers to a difference between adjacent beam angles when the beam angle is determined from the candidate beam angle range. For example, if the candidate beam angle range is [0°, 10°] and the angle interval is 1, the processing device 130 may determine the candidate beam angles as 0°, 1°, 2°, 3°, 4°, . . . , 10°, etc. The count of angles refers to a count of candidate beam angles that can be determined in the candidate beam angle range.

In 420, the processing device 130 (e.g., the first determination module 320 and the processor 210) may determine at leas one candidate collimator angle or at least one candidate lock field parameter based on the candidate beam angle range.

In some embodiments, as described in connection with FIG. 1, the collimator may include a primary collimator and a secondary collimator. The primary collimator may be used to define an initial range, an initial size, and/or an initial shape of the radiation beam. The secondary collimator may be used to further define the radiation beam, thereby defining a range, a size, and/or a shape of the radiation field formed by the radiation beam. For example, as shown in FIG. 5 (*b*), the secondary collimator may include upper and lower pairs of diaphragms (also referred to as jaws) that can be opened and closed. Accordingly, the collimator angle may reflect or affect the range, the size, and/or the shape of the radiation field (e.g., a white solid line square or a white dashed line square shown in FIG. 5 (*a*), a rectangle with diagonal shade shown in FIG. 5 (*b*)) formed by the radiation beam. In some embodiments, the collimator angle may include a rotation angle of the secondary collimator along a rotation axis (e.g., a mid-perpendicular of a plane where X1, X2, Y1, and Y2 is located in FIG. 5 (*b*)).

In some embodiments, for each of the at least one candidate beam angle in the candidate beam angle range, the processing device 130 may determine a candidate collimator angle corresponding to the candidate beam angle through geometry optimization. In some embodiments, the geometry optimization refers to optimization of a geometrical shape. In some embodiments, the geometry optimization refers to optimization of a projected geometrical shape of the ROI and/or the radiation field. In some embodiments, the geometry optimization may include a constrained optimization. For example, the constrained optimization may be constrained by a maximum angular variation range of the collimator (e.g., −90°~90°). As another example, the constrained optimization may be constrained by a count of leaves and a direction of movement of the leaves of the multi-leaf collimator. In some embodiments, the geometry optimization may include optimization of a cost function, for example, optimization of the cost function defined based on projection of the ROI.

In some embodiments, for each of the at least one candidate beam angle, the processing device 130 may determine the candidate collimator angle corresponding to the candidate beam angle through the geometry optimization based on a beam eyes view (BEV) projection of the ROI corresponding to the beam angle. For example, for each of the at least one candidate beam angle, the processing device 130 may determine the corresponding candidate collimator angle through geometry optimization based on an optimization parameter according to the BEV projection of the ROI corresponding to the beam angle. In some embodiments, the optimization parameter may include the direction of movement of the leaves of the collimator, the count of leaves, an area of the target area corresponding to the radiation field, an area of non-target area, a "geometric degree of freedom" of the beam, or the like, or any combination thereof. For example, the processing device 130 may adjust a ratio of a coverage of the radiation field for the non-target area to a coverage of the radiation field for the target area to be greater than a preset threshold (e.g., 85%, 90%, 95%) through the geometry optimization, and determine a corresponding collimator angle as the candidate collimator angle.

In some embodiments, as described in connection with above, the lock field parameter may reflect a locking position of the jaw (or diaphragm) of the collimator, for example, the positions of X1 and X2, and/or the positions of Y1 and Y2 in FIG. 5 (*a*) or FIG. 5 (*b*). In some embodiments, the lock field parameter may include an angle, an orientation, a coordinate, of the jaw, or the like, or any combination thereof.

In some embodiments, for each of the at least one candidate beam angle, the processing device 130 may determine a candidate lock field parameter corresponding to the candidate beam angle using a lock field parameter determination model. In some embodiments, the processing device 130 may determine the candidate lock field parameter corresponding to the candidate beam angle using the lock field parameter determination model based on an ROI projection and a radiation field projection corresponding to the candidate beam angle. In some embodiments, an input of the lock field parameter determination model may include the ROI projection and the radiation field projection corresponding to the candidate beam angle and an output of the lock field parameter determination model may be the lock field parameter. More information regarding the lock field parameter determination model may be found in FIG. 7 and the related descriptions thereof, which will not be repeated herein.

In some embodiments, for each of the at least one candidate beam angle, the processing device 130 may determine the candidate collimator angle and the candidate lock field parameter corresponding to the candidate beam angle using a radiation field information determination model. In some embodiments, the processing device 130 may determine the corresponding candidate collimator angle and the candidate lock field parameter based on the ROI projection and the radiation field projection corresponding to the candidate beam angle using the radiation field information determination model. In some embodiments, an input of the radiation field information determination model may include the ROI projection and the radiation field projection corresponding to the candidate beam angle and an output of the radiation field information determination model may be the collimator angle and the lock field parameter. More descriptions regarding the radiation field information determination model may be found in FIG. 8 and the related descriptions thereof, which will not be repeated herein.

In 430, the processing device 130 (e.g., the second determination module 330, the processor 210) may determine target radiation field information based on the at least one candidate collimator angle or the at least one candidate lock field parameter.

The radiation field information refers to a parameter related to a radiation field used to achieve a therapeutic purpose during the radiation therapy, such as the beam angle, the collimator angle, the lock field parameter, or the like, or any combination thereof. In some embodiments, the target radiation field information may include a target beam angle, a target collimator angle corresponding to the target beam angle, and a target lock field parameter corresponding to the target beam angle.

In some embodiments, for each of the at least one candidate beam angle, the processing device 130 may determine a candidate radiation field corresponding to the candidate beam angle based on the candidate collimator angle and/or the candidate lock field parameter corresponding to the candidate beam angle, and determine the target radiation field information based on the candidate radiation field. More descriptions may be found in FIG. 9 and the related descriptions thereof, which will not be repeated herein.

According to the embodiments of the present disclosure, the target radiation field information may be automatically determined based on the candidate collimator angle and the candidate lock field parameter, so that the impact of radiation field information on the effect of the treatment plan may be reduced and the preparation of the treatment plan may be integrated into the online automatic planning process, thereby contributing to the realization of a one-stop work-flow.

In some embodiments, the processing device 130 may determine a radiation treatment plan based on target radiation field information. For example, the processing device 130 may set the beam angle, the collimator angle, the lock field parameter, etc. in the treatment plan based on the target radiation field information, so as to determine the radiation treatment plan for the target object. As another example, the processing device 130 may individually optimize required radiation field information (e.g., add the collimator angle) for a preset preliminary target radiation field information that lacks part of the radiation field information (e.g., lack the collimator angle) based on the determined target radiation field information, so as to determine the radiation treatment plan. In some embodiments, the processing device 130 may automatically or semi-automatically determine the radiation treatment plan. For example, the processing device 130 may automatically determine the radiation treatment plan based on the target radiation field information. As another example, the processing device 130 may determine the radiation treatment plan based on the determined target radiation field information according to the radiation field optimization setting parameter set by medical staff. The radiation treatment plan may be determined based on the target radiation field information, which can shorten the time for preparing the radiation treatment plan and improve the quality of the treatment plan.

In some embodiments, the processing device 130 may obtain a first image corresponding to the target radiation field information and a second image of the object and determine adjusted radiation field information (e.g., second radiation field information) corresponding to the second image based on the target radiation field information, the relevant information of the first image and the second image. In some embodiments, the first image may be acquired under the target radiation field information. In some embodiments, the processing device 130 may update the treatment plan of the object based on the adjusted radiation field information. More descriptions may be found in FIGS. 10-15 and the related descriptions thereof, which will not be repeated herein.

It should be noted that the above description regarding the process 400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 400 may be accomplished with one or more additional operations not described and/or without one or more of the operations discussed above.

Figure 6:
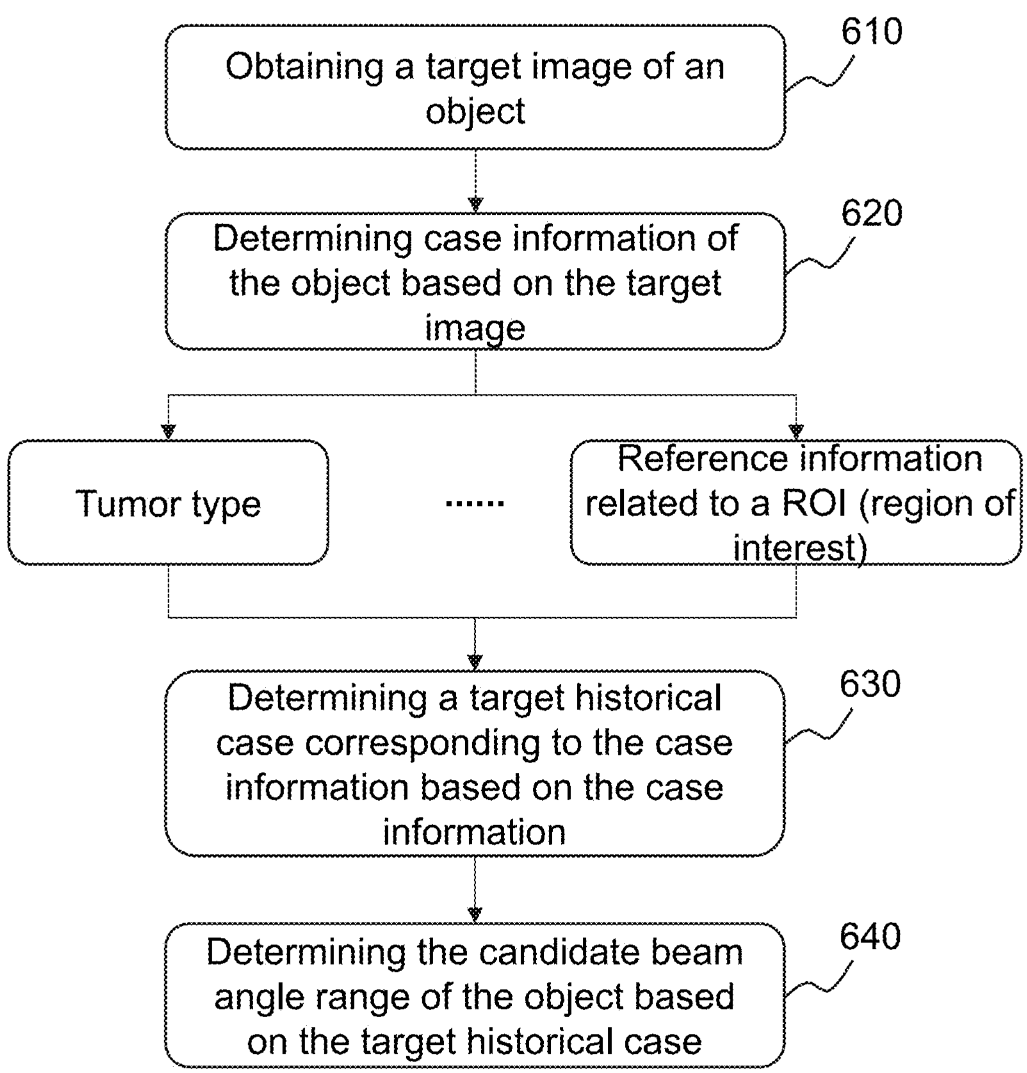
FIG. 6 is a flowchart illustrating an exemplary process for determining a candidate beam angle range according to some embodiments of the present disclosure.

FIG. 6 is a flowchart illustrating an exemplary process for determining a candidate beam angle range according to some embodiments of the present disclosure. In some embodiments, process 600 may be executed by the medical system 100. For example, the process 600 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 610, the processing device 130 (e.g., the obtaining module 310, the processor 210) may obtain a target image of an object.

The target image refers to a medical image containing a target area of the object to be treated. In some embodiments, the target image may include a 2D image, a 3D image, or a 4D image. In some embodiments, the target image may include a CT image, an MRI image, a PET image, an X-ray image, an ultrasound image, a radiotherapy radiation field image, or the like, or any combination thereof.

In some embodiments, the processing device 130 may obtain the target image of the object from a medical device (e.g., the medical device 110). In some embodiments, the processing device 130 may obtain the target image of the object from a storage device (e.g., the storage device 150), a database, or a medical system. For example, the processing device 130 may search the medical system and obtain the corresponding target image based on personal information, medical record information, etc. of the patient through the network 120. In some embodiments, the processing device 130 may obtain the target image in other ways and/or from other channels (e.g., provided by the patient), which is not limited in the present disclosure.

In 620, the processing device 130 (e.g., the obtaining module 310, the processor 210) may determine case information of the object based on the target image.

In some embodiments, as described in connection with the operation 410, the case information may include a tumor type and/or reference information related to a ROI.

In some embodiments, the processing device 130 may identify a tumor region and/or the ROI in the target image and further determine the tumor type and/or the reference information (e.g., a size, a position) related to the ROI. In some embodiments, the processing device 130 may automatically determine the case information based on the target image through a trained machine learning model.

In 630, the processing device 130 (e.g., the obtaining module 310, the processor 210) may determine a target historical case corresponding to the case information based on the case information.

In some embodiments, the processing device 130 may determine the target historical case based on a correlation between the case information (also referred to as current case information) of the object and historical case information. The correlation may reflect a degree of similarity between the historical case information and the current case information.

In some embodiments, the processing device 130 may search a database to determine the target historical case based on the current case information. For example, the processing device 130 may search the database (e.g., the storage device 150 or the medical system) based on the current case information to select a historical case with a tumor type similar to or the same as that of the current case, a historical case with reference information of the ROI similar to or the same as that of the current case, a historical cases with the tumor type and the reference information of the ROI similar to or the same as those of the current case, etc., and determine the selected historical case as the target historical case.

In 640, the processing device 130 (e.g., the obtaining module 310, the processor 210) may determine the candidate beam angle range of the object based on the target historical case.

In some embodiments, the processing device 130 may determine the candidate beam angle range based on a treatment plan of the target historical case. For example, if the tumor type of a current patient is a breast tumor, the processing device 130 may retrieve the database to obtain a historical breast tumor case, determine at least one beam angle corresponding to the historical breast tumor case, and determine the candidate beam angle range based on the at least one beam angle.

In some embodiments, the processing device 130 may determine the candidate beam angle range through a trained machine learning model. For example, the processing device 130 may use scanning images corresponding to various cases in historical radiotherapy data and the corresponding radiation field information as training samples to obtain the corresponding model. Accordingly, the processing device 130 may input the target image into the trained machine learning model to determine the candidate beam angle range.

According to the embodiments of the present disclosure, the candidate beam angle range may be determined based on the correlation between the current case information of the object and the historical medical case information, which can reduce the complexity of preparing the treatment plan and avoid errors or unreasonable phenomena caused by manual settings.

In some embodiments, the processing device 130 may adjust the candidate beam angle range based on a user instruction.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above.

Figure 7:
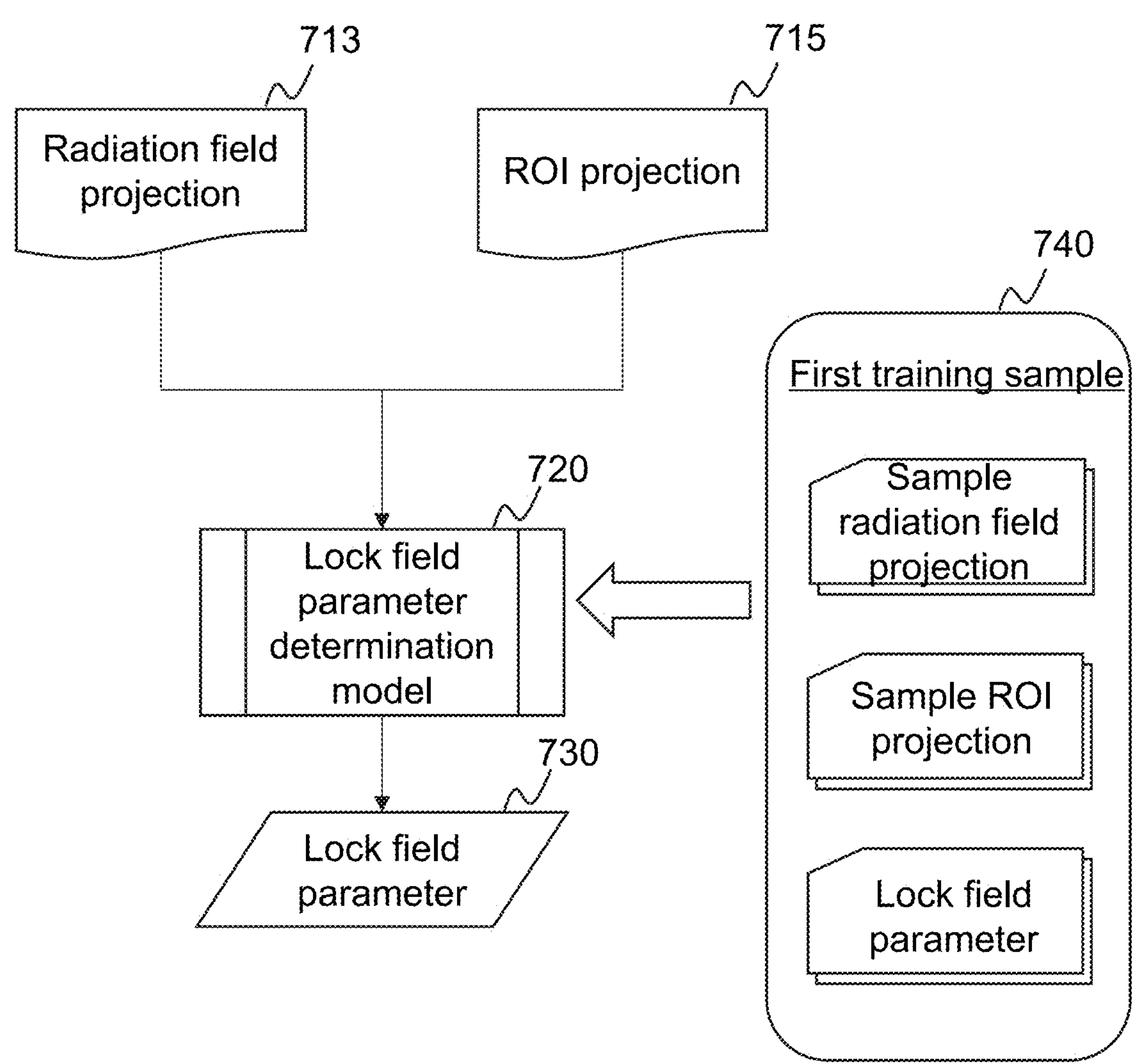
FIG. 7 is a flowchart illustrating an exemplary process for determining a lock field parameter according to some embodiments of the present disclosure.

FIG. 7 is a flowchart illustrating an exemplary process for determining a lock field parameter according to some embodiments of the present disclosure. In some embodiments, process 700 may be executed by the medical system 100. For example, the process 700 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In 713, the processing device 130 (e.g., the first determination module 320, the processor 210) may obtain a radiation field projection corresponding to the candidate beam angle.

The radiation field projection may reflect geometric information (e.g., a geometrical shape) of a radiation field. In some embodiments, the radiation field projection may include a projection of the beam angle on a BEV plane. In some embodiments, the processing device 130 may determine the radiation field projection corresponding to each of the at least one candidate beam angle. For example, the processing device 130 may respectively project each of the at least one candidate beam angle onto the BEV plane, so as to determine the corresponding radiation field projection.

In 715, the processing device 130 (e.g., the first determination module 320, the processor 210) may obtain an ROI projection.

In some embodiments, as described in connection with the above, the ROI projection may reflect the geometric information of a target area and/or an OAR. In some embodiments, the ROI projection may include a projection of the target area and/or a projection of the OAR on the BEV plane.

In some embodiments, the processing device 130 may obtain the ROI projection of an object based on a target image. In some embodiments, the processing device 130 may obtain the ROI projection by marking the target image. For example, the processing device 130 may mark a tumor region and the OAR in the target image of the object and project the marked ROI on the BEV plane, so as to determine the ROI projection.

In 720, the processing device 130 (e.g., the first determination module 320, the processor 210) may input the radiation field projection and the ROI projection into a lock field parameter determination model.

In some embodiments, for each of the at least one candidate beam angle, the processing device 130 may input the ROI projection and the radiation field projection into the lock field parameter determination model to determine a candidate lock field parameter corresponding to the candidate beam angle.

In some embodiments, the lock field parameter determination model may include a trained machine learning model. For example, the machine learning model may include a convolutional neural network (CNN) model, a fully connected neural network model, a recurrent neural network (RNN) model, etc.

In 730, the processing device 130 (e.g., the first determination module 320, the processor 210) may determine the candidate lock field parameter.

In some embodiments, the lock field parameter determination model may output the lock field parameter by analyzing and processing the input radiation field projection and the ROI projection. For example, the lock field parameter determination model may analyze and process the ROI projection and the radiation field projection corresponding to each candidate beam angle and output the lock field parameter corresponding to a current candidate beam angle. In some embodiments, the processing device 130 may determine the lock field parameter output by the lock field parameter determination model as the candidate lock field parameter of the candidate beam angle.

In some embodiments, the lock field parameter determination model may be trained based on a plurality of training samples. As illustrated in 740, the lock field parameter determination model may be determined by training a preliminary machine learning model based on a plurality of first training samples.

In some embodiments, each first training sample may include a sample radiation field projection, a sample ROI projection, and a corresponding lock field parameter. In some embodiments, the plurality of first training samples may include a plurality of lesion types. For example, the processing device 130 may obtain historical radiotherapy data (e.g., a historical treatment plan) of various types of sample cases such as a breast tumor, a lung tumor, a uterine tumor, a gastric tumor, an epithelial tumor, a mesenchymal tumor, a neurogenic tumor, a lymphoid tumor, etc., and accordingly determine the plurality of first training samples.

In some embodiments, the processing device 130 may use the sample radiation field projection and the sample ROI projection of the plurality of first training samples as an input of the model training and the lock field parameter corresponding to the radiation field as a label and train a first preliminary model to obtain a trained lock field parameter determination model. In some embodiments, the processing device 130 may train the lock field parameter determination model in any reasonable and feasible way, which is not limited in the present disclosure.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 700 may be accomplished with one or more additional operations not described and/or without one or more of the operations discussed above.

Figure 8:
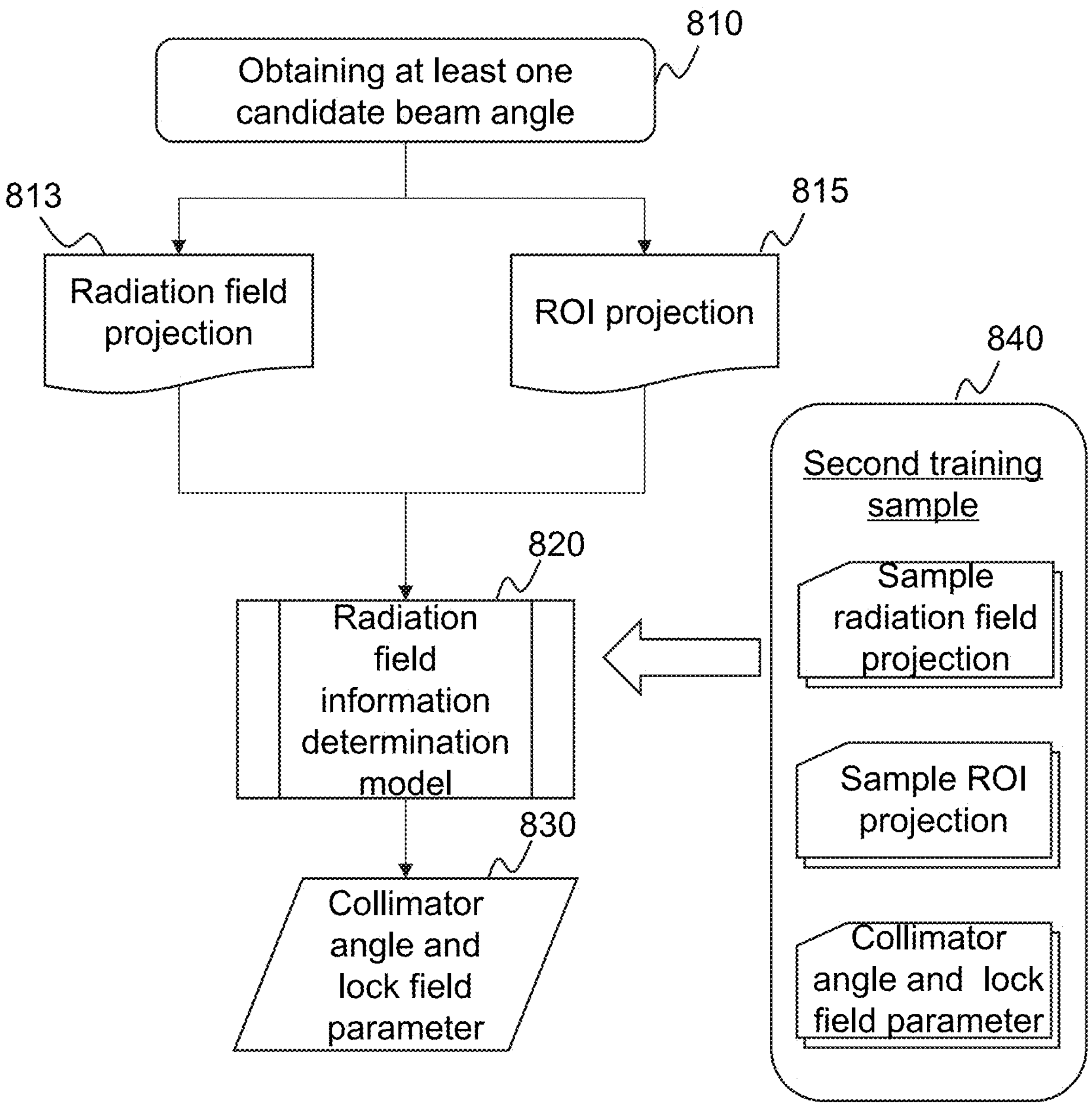
FIG. 8 is a flowchart illustrating an exemplary process for determining radiation field information according to some embodiments of the present disclosure.

FIG. 8 is a flowchart illustrating an exemplary process for determining radiation field information according to some embodiments of the present disclosure. In some embodiments, process 800 may be executed by the medical system 100. For example, the process 800 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

As shown in FIG. 8, in some embodiments, for each of the at least one candidate beam angle, the processing device 130 may determine a candidate collimator angle and a candidate lock field parameter corresponding to the candidate beam angle using a radiation field information determination model.

In 810, the processing device 130 may obtain at least one candidate beam angle based on a candidate beam angle range of the object. More descriptions regarding the candidate beam angle range may be found in FIG. 4 and/or FIG. 6 and the related descriptions thereof, which will not be repeated herein.

In 813, for each of the at least one candidate beam angle, the processing device 130 may determine a corresponding radiation field projection. More descriptions may be found in the operation 713 and the descriptions thereof.

In 815, the processing device 130 may obtain an ROI projection. More descriptions may be found in the operation 715 and the descriptions thereof.

In 820, for each of the at least one candidate beam angle, the processing device 130 may input the radiation field projection and the ROI projection into the radiation field information determination model.

In 830, the processing device 130 may determine the candidate collimator angle and the candidate lock field parameter corresponding to the candidate beam angle.

In some embodiments, the radiation field information determination model may output a corresponding collimator angle and a lock field parameter by analyzing and processing the input radiation field projection and ROI projection. For example, the radiation field information determination model may analyze and process the ROI projection and the radiation field projection corresponding to each candidate beam angle and output the collimator angle and the lock field parameter corresponding to the candidate beam angle. In some embodiments, the processing device 130 may determine the collimator angle and the lock field parameter output by the radiation field information determination model as the candidate collimator angle and the candidate lock field parameter of the candidate beam angle.

In some embodiments, the radiation field information determination model may be trained based on a plurality of training samples. As illustrated in 840, the radiation field information determination model may be determined by training a preliminary machine learning model (e.g., a CNN model, a full connection neural network model, a RNN model) based on a plurality of second training samples.

In some embodiments, each second training sample may include a sample radiation field projection, a sample ROI projection, the collimator angle, and the lock field parameter. In some embodiments, the plurality of second training samples may include a plurality of lesion types. For example, the processing device 130 may obtain treatment data corresponding to a plurality of different types of radiotherapy cases and accordingly determine the plurality of second training samples.

In some embodiments, the first training sample and the second training sample may correspond to the same sample case or different sample cases. In some embodiments, the first training sample and the second training sample may correspond to the same radiotherapy data or different radiotherapy data.

In some embodiments, the processing device 130 may use the sample radiation field projection and the sample ROI projection of the plurality of second training samples as an input of the model training and the collimator angle and the lock field parameter corresponding to the radiation field as a label and train a second preliminary model to obtain a trained radiation field information determination model. In some embodiments, the processing device 130 may train the radiation field information determination model in any reasonable and feasible way to obtain the radiation field information determination model, which is not limited in the present disclosure.

In some embodiments, the lock field parameter determination model and the radiation field information determination model may be obtained through the same training way or different training ways. In some embodiments, the lock field parameter determination model and the radiation field information determination model may be trained simultaneously, jointly, or separately.

The corresponding candidate collimator angle and candidate lock field parameter may be automatically determined using the machine learning model based on the candidate beam angle range, which can improve the efficiency and accuracy of radiation field information formulation.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 800 may be accomplished with one or more additional operations not described and/or without one or more of the operations discussed above.

FIG. 9 is a flowchart illustrating an exemplary process for determining target radiation field information according to some embodiments of the present disclosure. In some embodiments, process 900 may be executed by the medical system 100. For example, the process 900 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 900. The operations of the illustrated process presented below are intended to be illustrative. In some embodiments, the process 900 may be accomplished with one or more additional operations not described and/or without one or more of the operations discussed. Additionally, the order of the operations of process 900 illustrated in FIG. 9 and described below is not intended to be limiting.

In 910, for each of the at least one candidate beam angle, the processing device 130 (e.g., the second determination module 330, the processor 210) may determine a candidate radiation field corresponding to the candidate beam angle based on a candidate collimator angle and/or a candidate lock field parameter corresponding to the candidate beam angle.

In some embodiments, the processing device 130 may determine the candidate beam angle and the candidate collimator angle and the candidate lock field parameter corresponding to the candidate beam angle as a set of candidate radiation field. For the at least one candidate beam angle, the processing device 130 may determine at least one candidate field corresponding to the at least one candidate beam angle respectively. Accordingly, information of each candidate radiation field may include the candidate beam angle, the candidate collimator angle corresponding to the candidate beam angle, and the candidate lock field parameter corresponding to the candidate beam angle.

In 920, the processing device 130 (e.g., the second determination module 330, the processor 210) may determine the target radiation field information using a fluence map optimization-based multi-stage optimization approach based on at least one candidate radiation field corresponding to the at least one candidate beam angle.

In some embodiments, the processing device 130 may determine the target radiation field information using the fluence map optimization (FMO)-based multi-stage optimization approach based on the at least one candidate radiation field corresponding to at least one candidate beam angle.

The fluence map may represent an expected intensity distribution of a beam that is planned to be delivered to a target volume of an object in radiation therapy. The FMO refers to determining an "optimal" set of beam intensities that satisfy constraint (e.g., dose constraint) through an iterative optimization manner. For example, through the FMO, a radiation dose of the treatment plan may be delivered to an irradiated target area (e.g., a planning target volume (PTV), a tumor area) without exceeding a maximum tolerable dose of an area avoiding irradiation (e.g., an OAR).

In some embodiments, the FMO may include any feasible iterative optimization manner such as an alternating direction manner based on a multiplier, a Chambolle-Pock algorithm, an accelerated proximal gradient manner, etc., which is not limited in the present disclosure. Further, the FMO-based multi-stage optimization refers to two or more stages of optimization of the radiation field based on fluence map optimization. For example, a multi-stage optimization process may include: a first stage of greed-like sparseness and a second stage of simplex local optimization.

In some embodiments, for each candidate beam angle in a candidate beam angle range, the processing device 130 may perform the FMO-based multi-stage optimization based on the corresponding candidate radiation field, select an optimal radiation field parameter combination that meets an optimization parameter condition (which may be a system default value or may be set by a user), and determine the optimal radiation field parameter combination (e.g., a combination of an optimal field angle, an optimal collimator angle, and an optimal lock field parameter) as the target radiation field information. In some embodiments, the radiation field determined based on the optimal radiation field parameter combination may enable the radiation dose of the treatment plan to be delivered to the irradiation target area and avoid irradiation of the OAR. For example, for the radiation field determined based on the optimal radiation parameter combination, a coverage of the target area meets a clinical requirement, and the irradiation to normal tissues may be minimized.

In some embodiments, the processing device 130 may determine two or more radiation field parameter combinations based on the at least one candidate radiation field and determine the two or more radiation field parameter combinations as the target radiation field information. For example, the processing device 130 may sort parameter combinations corresponding to the candidate radiation fields according to a preset condition and determine the radiation field parameter combinations corresponding to the top three candidate radiation fields as the target radiation field information.

In some embodiments, the processing device 130 may perform the beam angle optimization and the collimator angle optimization simultaneously or separately (where the optimization mode(s) may be system default or set by the user). In some embodiments, the processing device 130 may perform the collimator angle optimization and the lock field parameter optimization simultaneously or separately (where the optimization mode(s) may be system default or set by the user). Merely by way of example, the processing device 130 may select at least one optimal field angle from the candidate beam angle range by performing the FMO-based multi-stage optimization based on an optimization parameter condition (which may be a system default or set by a user) for field angle, and determine at least one optimal collimator angle and/or at least one optimal lock field parameter corresponding to the at least one optimal field angle by performing a further optimization operation (e.g., collimator angle optimization, lock field parameter optimization).

It should be noted that the above description regarding the processes 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
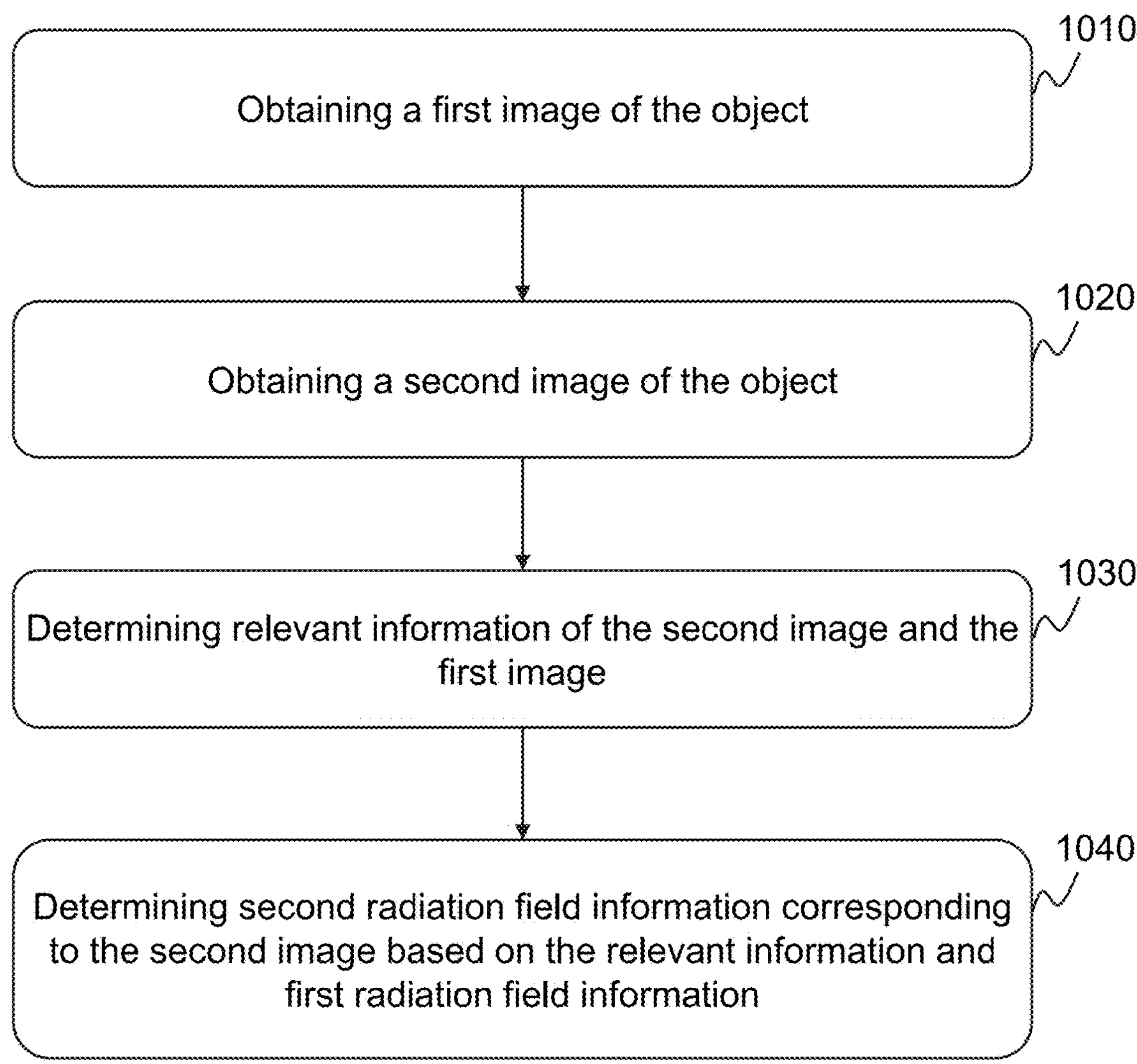
FIG. 10 is a flowchart illustrating an exemplary process for determining second radiation field information according to some embodiments of the present disclosure.

FIG. 10 is a flowchart illustrating an exemplary process for determining second radiation field information according to some embodiments of the present disclosure. In some embodiments, process 1000 may be executed by the medical system 100. For example, the process 1000 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 1000. The operations of the illustrated process presented below are intended to be illustrative. In some embodiments, the process 1000 may be accomplished with one or more additional operations not described and/or without one or more of the operations discussed. Additionally, the order of the operations of process 1000 illustrated in FIG. 10 and described below is not intended to be limiting.

In 1010, the processing device 130 (e.g., an adjusted radiation field information determination module, the processor 210) may obtain a first image of the object.

Generally, a radiation therapy course may be performed in a plurality of sessions and an interval between two radiation treatments may be 1 day, 2 days, 1 week, etc. In some embodiments, the first image may include a medical image collected when a patient is diagnosed with a lesion, a medical image collected when a treatment plan is initially formulated, or a medical image collected after a previous radiation treatment is completed. For example, the first image may be a medical image collected when the patient is diagnosed with the lesion.

In some embodiments, the first image may include a 2D image, a 3D image, or a 4D image. In some embodiments, the first image may include a CT image, an MRI image, a PET image, a functional magnetic resonance imaging (fMRI) image, an X-ray image, an ultrasound image, a radiotherapy radiation field image, a SPECT image, etc. In some embodiments, the first image may include time information (e.g., time information of image collection). Accordingly, the first image may be understood as a collection of a plurality images corresponding to a plurality of time points or periods of time.

In some embodiments, the first image may include first target area information of the object and/or first OAR information (also can be collectively referred to as “ROI information” or “reference information related to the ROI”). In some embodiments, the target area information may include an anatomical structure of the target area, a position of the target area, a type of the target area, a size of the target area, or the like, or any combination thereof. The type of the target area refers to a type of an organ corresponding to the target area (e.g., prostate, breast). In some embodiments, the OAR information may include a position, a type, a size of the OAR, or the like, or any combination thereof.

In some embodiments, the processing device 130 may obtain the first image from a medical device. For example, the processing device 130 may obtain the first image collected by the medical device 110 when determining the target radiation field information of the object. In some embodiments, the processing device 130 may obtain the first image from a storage device (e.g., the storage device 150), a database, or a medical system. For example, the processing device 130 may search the medical system and obtain the corresponding first image based on personal information, medical record information, target radiation field information, etc. of the patient through the network 120.

In 1020, the processing device 130 (e.g., the adjusted radiation field information determination module, the processor 210) may obtain a second image of the object.

The second image may be a medical image collected after the first image. For example, the second image may be a medical image collected when the patient is subjected to a current radiation treatment (e.g., the day of radiation treatment). In some embodiments, an interval between collection times of the second image and the first image may be two days, one week, two weeks, one month, etc. In some embodiments, the second image may be a medical image obtained after one radiation treatment session, two radiation treatment sessions, half a course of radiation treatment, etc. In some embodiments, the second image may be a medical image collected just before a first radiation treatment session.

In some embodiments, the second image may include a 2D image, a 3D image, or a 4D image. In some embodiments, the second image may include a CT image, an MRI image, a PET image, an fMRI image, an X-ray image, an ultrasound image, a radiotherapy radiation field image, a SPECT image, etc. In some embodiments, the second image may include time information (e.g., time information of image collection). Accordingly, the second image may be understood as a collection of a plurality images corresponding to a plurality time points or periods of time.

In some embodiments, the second image may include second target area information and/or second OAR information of the object. In some embodiments, at least one of the first image or the second image may be an anatomical image. In some embodiments, one of the first image and the second image may be an anatomical image and the other one may be a functional image.

In some embodiments, the processing device 130 may obtain the second image from the medical device. For example, the processing device 130 may obtain a scanning image generated by the medical device 110 scanning the object and determine the scanning image as the second image. In some embodiments, the processing device 130 may obtain the second image from the storage device (e.g., the storage device 150), the database, or the medical system. For example, the processing device 130 may search the medical system and obtain the corresponding second image based on the personal information, the medical record information, etc. of the patient through the network 120. In some embodiments, the processing device 130 may obtain the first image and/or the second image in other ways and/or from other channels (e.g., provided by the patient), which is not limited in the present disclosure.

In 1030, the processing device 130 (e.g., the adjusted radiation field information determination module, the processor 210) may determine relevant information of the second image and the first image.

The relevant information may reflect a similarity or association between the second image and the first image. In some embodiments, the relevant information may include a registration parameter and/or a target area projection similarity. In some embodiments, the registration parameter may include a rigid registration parameter and/or a non-rigid registration parameter.

The rigid registration refers a process in which one image (e.g., the first image) of the images (e.g., the first image and the second image) to be registered is set as a reference image (also can be referred to as a standard image) and the other image (also can be referred to as a floating image, e.g., the second image) is spatially transformed according to the standard image (e.g., after a predetermined count of rotations, translations), so that corresponding pixels in the floating image and the standard image achieve consistent in spatial positions. Accordingly, the rigid registration parameter may reflect a spatial transformation relationship (e.g., a rotation angle, a translation distance) between the two images. In some embodiments, the rigid registration parameter may include a parameter such as a horizontal displacement, a vertical translation, a rotation angle, etc. during the rigid registration process. In some embodiments, the rigid registration parameter may be expressed in a numerical value, a vector, a matrix, etc.

In some embodiments, the processing device 130 may determine the rigid registration parameter based on anatomical structures in the first image and the second image. In some embodiments, the processing device 130 may determine the rigid registration parameter by performing the rigid registration on the second image and the first image. For example, the processing device 130 may determine the first image as the standard image and perform a spatial transformation on the second image according to the first image, so as to determine the rigid registration parameter. In some embodiments, a rigid registration manner may include any reasonable and feasible manner (e.g., rigid body transformation, affine transformation, projection transformation), which is not limited in the present disclosure.

The non-rigid registration refers to a process of spatially transforming the floating image (e.g., the second image) with irregular internal deformation according to the standard image (e.g., the first image). Accordingly, the non-rigid registration parameter refers to a transformation parameter (e.g., a geometric shape change of organ tissue(s) or the target area of radiation therapy) corresponding to a deformed part in a medical image when the medical image is registered. Generally, a spontaneous and voluntary movement of the radiation therapy tissue(s) or organ(s) may cause a change in a size, a shape, a volume, etc. of the tissue(s) and/or the organ(s), resulting in some irregular internal deformation in the collected medical images. For example, the radiation therapy may usually require a plurality of courses, the shape and/or the size of the target area (e.g., a tumor area) may gradually change (e.g., the target area may gradually become smaller as gradually treated) as each course ends, which may inevitably lead to a certain deformation of the target area between images acquired in the courses. Accordingly, the non-rigid registration parameter may include a deformation registration parameter of the target area.

In some embodiments, the processing device 130 may determine the non-rigid registration parameter based on the anatomical structures in the first image and the second image. In some embodiments, the processing device 130 may determine the non-rigid registration parameter by performing the non-rigid registration on the second image and the first image. In some embodiments, a non-rigid registration manner may include a spline-based registration manner, a physical model-based registration manner, an optical flow field model-based registration manner, etc., which is not limited in the present disclosure.

The target area similarity may reflect a degree of similarity of geometrical shapes of the target areas in the first image and the second image.

In some embodiments, the target area similarity may include a rough similarity between the target areas in the first image and the second image. For example, the first image may be a medical image collected after a previous radiation treatment and the second image may be a medical image collected before or after a next radiation treatment. Due to the radiation therapy, the shape, the size, etc. of the target areas in the two collected medical images may have changed (e.g., the target area may have become smaller after the radiation therapy). In this case, the target area similarity refers to a rough similarity between the target area in the first image and the target area in the second image (e.g., whether centerlines of the two target areas are at a similar tissue position, whether the two target areas contain similar tissue). Merely by way of example, as shown in FIG. 13, (a) represents a target area projection of the first image under a BEV plane and (b) represents a target area projection of the second image under the BEV plane, it can be seen from the target area projection in the figures that with completion of successive radiation treatments, target area A and target area B in (b) (i.e., the second image) are obviously smaller in size than target area A and target area in (a) (i.e., the first image), and shapes also change to some extent.

In some embodiments, the target area similarity may include a target area projection similarity (e.g., a target area projection similarity under the BEV plane). The target area projection similarity may reflect a smoothness of a deformation field between two objects to be registered (e.g., between the target area corresponding to the first image and the target area corresponding to the second image). The smoother the deformation field is, the closer the two objects (e.g., the two target area projections) may be. For example, the target area projection similarity between the second image and the first image may be a rough similarity between target area projection A or B in FIG. 13 (*b*) and target area projection A or B in FIG. 13 (*a*).

In some embodiments, the target area projection similarity may be determined based on a deformation registration relationship between the target area projection corresponding to the first image and the target area projection corresponding to the second image.

In some embodiments, the rigid registration parameter may include a rigid registration parameter of the target area projection. The non-rigid registration parameter may include a non-rigid registration parameter of the target area projection (e.g., the deformable registration parameter).

In 1040, the processing device 130 (e.g., the adjusted radiation field information determination module, the processor 210) may determine second radiation field information corresponding to the second image based on the relevant information and first radiation field information corresponding to the first image.

In some embodiments, the processing device 130 may determine an initial beam angle corresponding to the second image based on the rigid registration parameter of the second image and the first image and a first beam angle of the first radiation field information corresponding to the first image. The processing device 130 may determine the first radiation field information based on the first image. Further, the processing device 130 may determine a second beam angle corresponding to the second image by adjusting the initial beam angle based on the target area projection similarity of the second image and the first image. In some embodiment, the first radiation field information or the second radiation field information may include a beam angle, a collimator angle, a lock field parameter, or the like, or any combination thereof. More descriptions regarding the determining the second beam angle may be found in FIGS. 11-13 and the related descriptions thereof, which will not be repeated herein.

In some embodiments, the processing device 130 may determine a second collimator angle corresponding to the second image based on the rigid registration parameter of the second image and the first image and a first collimator angle (e.g., target collimator angle) of the first radiation field information. More descriptions may be found in FIG. 11 and the related descriptions thereof, which will not be repeated herein.

In some embodiments, the processing device 130 may determine a second lock field parameter corresponding to the second image based on the non-rigid registration parameter of the second image and the first image and a first lock field parameter (e.g., target lock field parameter) of the first radiation field information. More descriptions may be found in FIG. 11 and the related descriptions thereof, which will not be repeated herein.

In some embodiments, when the first radiation field information is an optimal radiation field parameter combination, accordingly, the processing device 130 may determine a set of second radiation field parameters (e.g., as the adjusted radiation field information) consisting of one second beam angle, one corresponding second collimator angle, and one second lock field parameter. When the first radiation field information contains two or more sets of radiation field parameter combinations (e.g., the radiation field parameter combinations corresponding to the top three candidate fields), accordingly, the processing device 130 may determine two or more sets of second radiation field parameters and each set of second field adjustment parameters may include one second beam angle, one second collimator angle, and one second lock field parameter.

In some implementations, the processing device 130 may first determine the second beam angle, then determine the second collimator angle, and further determine the second lock field parameter. For example, after determining the second collimator angle based on the second beam angle, the processing device 130 may further determine the second lock field parameter based on the deformation registration parameter of the target area projection of the second image and the target area projection of the first image under the second beam angle and the first lock field parameter.

In some implementations, the processing device 130 may simultaneously determine the second beam angle, the second collimator angle, and the second lock field parameter corresponding to the second image. For example, the processing device 130 may determine the corresponding second collimator angle and the corresponding second lock field parameter while determining the second beam angle.

In some embodiments, the beam angle, the collimator angle, and the lock field parameter may be adjusted separately, simultaneously, or only one or two of the beam angles, the collimator angle, and the lock field parameter may be adjusted.

According to the embodiments of the present disclosure, the second radiation field information corresponding to the second image may be determined based on the target area information and the OAR information between the first image and the second image, the change information of the target area and the OAR in the first image and the second image may be integrated into the process for determining the radiation field information, which can not only avoid deviation of the radiation field information caused by the deformation of the target area and/or the OAR, but also avoid the risk of an error caused by manual setting of the radiation field information and prolonging a time of a radiotherapy workflow, thereby improving the accuracy of an adjustment result of the radiation field information.

In some embodiments, the processing device 130 may adjust the second radiation field information based on an adjustment instruction. For example, the processing device 130 may receive the adjustment instruction input by a user through the terminal device 140 and adjust the second beam angle, the second collimator angle, or the second lock field parameter based on the adjustment instruction. The second radiation field information may be adjusted based on the adjustment instruction of the user, which can avoid mismatching between the automatically determined radiation field information and the actual situation and improve the accuracy and matching of the radiation field information setting.

In some embodiments, the processing device 130 may determine a similarity between the second image and the first image, and provide a notification in response to a determination that the similarity is smaller than a preset threshold. For example, when determining that the similarity between the second image and the first image is smaller than the preset threshold, the processing device 130 may provide the notification to the terminal device 140 to notify the user. According to the notification, the processing device 130 or the user may determine whether the treatment plan needs to be adjusted, or whether the patient is positioned incorrectly, or whether there is an error in the image collection process, etc., so as to avoid the deviation of the determined second radiation field information due to the second image collection error, thereby improving the effectiveness of radiation therapy.

In some embodiments, the processing device 130 may update the treatment plan of the object based on the second radiation field information (as mentioned above, the treatment plan may be determined based on the first radiation field information (e.g., the target radiation field information)). In some embodiments, the processing device 130 may update the treatment plan of the object using an updating model based on the second radiation field information. More descriptions may be found in FIG. 14 and the related descriptions thereof, which will not be repeated herein.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above.

Figure 11:
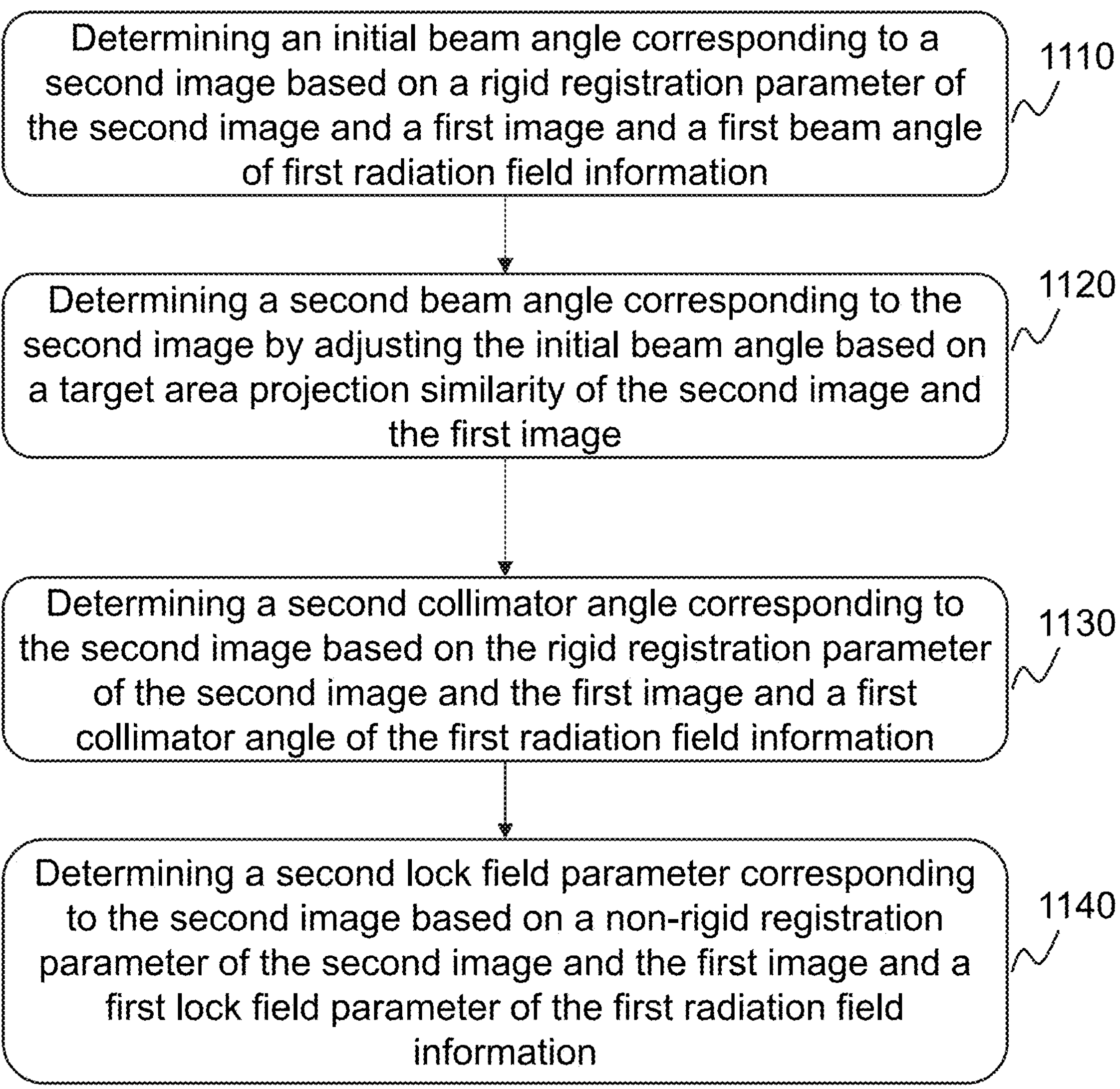
FIG. 11 is a flowchart illustrating an exemplary process for determining second radiation field information according to other embodiments of the present disclosure.

FIG. 11 is a flowchart illustrating an exemplary process for determining second radiation field information according to other embodiments of the present disclosure. In some embodiments, process 1100 may be executed by the medical system 100. For example, the process 1100 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 1100. The operations of the illustrated process presented below are intended to be illustrative. In some embodiments, the process 1100 may be accomplished with one or more additional operations not described and/or without one or more of the operations discussed. Additionally, the order of the operations of process 1100 illustrated in FIG. 11 and described below is not intended to be limiting.

In 1110, the processing device 130 (e.g., an adjusted radiation field information determination module, the processor 210) may determine an initial beam angle corresponding to a second image based on a rigid registration parameter of the second image and a first image and a first beam angle of first radiation field information.

In some embodiments, the processing device 130 may determine the initial beam angle by spatially transforming the first beam angle (e.g., target beam angle) based on the rigid registration parameter of the second image and the first image. Merely by way of example, after rigidly registering the second image and the first image, if there is a rotation relationship between the second image and the first image, the processing device 130 may transform the first beam angle (e.g., rotate the target beam angle according to the rigid registration matrix) using a corresponding rigid registration matrix when the second image is spatially transformed and use the transformed first beam angle as the initial beam angle corresponding to the second image.

In 1120, the processing device 130 (e.g., the adjusted radiation field information determination module, the processor 210) may determine a second beam angle corresponding to the second image by adjusting the initial beam angle based on a target area projection similarity of the second image and the first image.

In some embodiments, the processing device 130 may determine an initial angle adjustment range based on the initial beam angle, and determine the second beam angle by updating the initial angle adjustment range based on the target area projection similarity of the second image and the first image. In some embodiments, when a range difference between the initial angle adjustment range and the updated angle adjustment range is smaller than a preset value, the processing device 130 may determine the second beam angle (or the second beam angle range). More descriptions may be found in FIG. 12 and the related descriptions thereof, which will not be repeated herein.

In 1130, the processing device 130 (e.g., the adjusted radiation field information determination module, the processor 210) may determine a second collimator angle corresponding to the second image based on the rigid registration parameter of the second image and the first image and a first collimator angle of the first radiation field information.

The rigid registration parameter of the second image and the first image may include the rigid registration parameter of the target area projection. In some embodiments, the processing device 130 may determine the rigid registration parameter of the target area projection by performing a rigid registration on the target area projection of the first image and the target area projection of the second image. In some embodiments, the processing device 130 may determine the rigid registration parameter of the target area projection by performing the rigid registration on the target area projection of the first image and the target area projection of the second image under a BEV plane. For example, FIG. 13 (*a*) shows the target area projection A and B corresponding to the first image and FIG. 13 (*b*) shows the target area projection A and B corresponding to the second image. The processing device 130 may determine the rigid registration parameter by performing the rigid registration on the target area A (or target area B) in FIG. 13 (*a*) and the target area A (or target area B) in FIG. 13 (*b*).

In some embodiments, the processing device 130 may determine the second collimator angle corresponding to the second image by performing a spatial transformation on the first collimator angle (e.g., target collimator angle) based on the rigid registration parameter of the target area projection. Merely by way of example, for each beam angle in the treatment plan, the processing device 130 may determine the target area projection B1 of the first image on the BEV plane at the first beam angle (e.g., target beam angle) and the target area projection B2 of the second image on the BEV plane at the corresponding second beam angle, perform a rigid registration on the target area projection B1 and the target area projection B2, perform a spatial transformation on the first collimator angle using a rigid registration matrix corresponding to the target area projection B1 and the target area projection B2, and determine the transformed first collimator angle as the second collimator angle corresponding to the second image. For example, as shown in FIG. 5 (*a*), a white dashed line square in the figure indicates a radiation field formed by the first collimator angle and a white solid line square indicates a radiation field formed by the second collimator angle.

In 1140, the processing device 130 (e.g., the adjusted radiation field information determination module, the processor 210) may determine a second lock field parameter corresponding to the second image based on the non-rigid registration parameter of the second image and the first image and a first lock field parameter of the first radiation field information.

In some embodiments, the non-rigid registration parameter may include a deformation registration parameter of the target area projection. In some embodiments, the processing device 130 may determine the non-rigid registration parameters of the target area projection by performing a non-rigid registration on the target area projection of the first image and the target area projection of the second image. In some embodiments, the processing device 130 may determine a first target area projection of the first image on the BEV plane at the first beam angle, and a second target area projection of the second image on the BEV plane at the corresponding second beam angle. Further, the processing device 130 may determine the non-rigid registration parameter of the target area projection by performing the non-rigid registration on the first target area projection and the second target area projection.

In some embodiments, the processing device 130 may determine jaw lock information by transforming the first lock field parameter (e.g., target lock field parameter) based on the deformation registration parameter of the target area projection. Further, the processing device 130 may determine the second lock parameter using a linear fitting algorithm based on the jaw lock information. Merely by way of example, for the first beam angle and the second beam angle that match each other, the processing device 130 may determine the deformation registration parameter of the target projection of the first image and the second image, and obtain the jaw lock information (e.g., a coordinate) by transforming the first lock field parameter corresponding to the first beam angle to the BEV plane of the second image based on the deformation registration parameter of the target projection (e.g., a deformation field). Further, according to a linear fitting algorithm, the processing device 130 may select a straight line parallel to an X direction as a locking position (e.g., X1 and X2 in FIG. 5 (*a*)) of a Y jaw corresponding to the second image and further determine a locking position (e.g., Y1 and Y2 in FIG. 5 (*a*)) of a X jaw based on the locking position of the Y jaw, so as to determine the second lock field parameter. Alternatively, according to a linear fitting algorithm, the processing device 130 may select a straight line parallel to the Y direction as the locking position of the X jaw corresponding to the second image and further determine the locking position of the Y jaw based on the locking position of the X jaw, so as to determine the second lock field parameter.

According to the embodiments of the present disclosure, the collimator angle may be adjusted based on the rigid registration parameter of the target area projection, and the jaw locking position may be adjusted based on the deformation registration parameter of the target area projection, which can reduce the impact of deformation and/or rotation of the target area on the radiation field, thereby improving the treatment effect.

It should be noted that the above description regarding the process 1100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 130 may execute the operation 1120, the operation 1130, and the operation 1140, simultaneously, or first execute the operation 1140 and then execute the operation 1130, or at least one of the operation 1120, the operation 1130, and the operation 1140 may be omitted.

Figure 12:
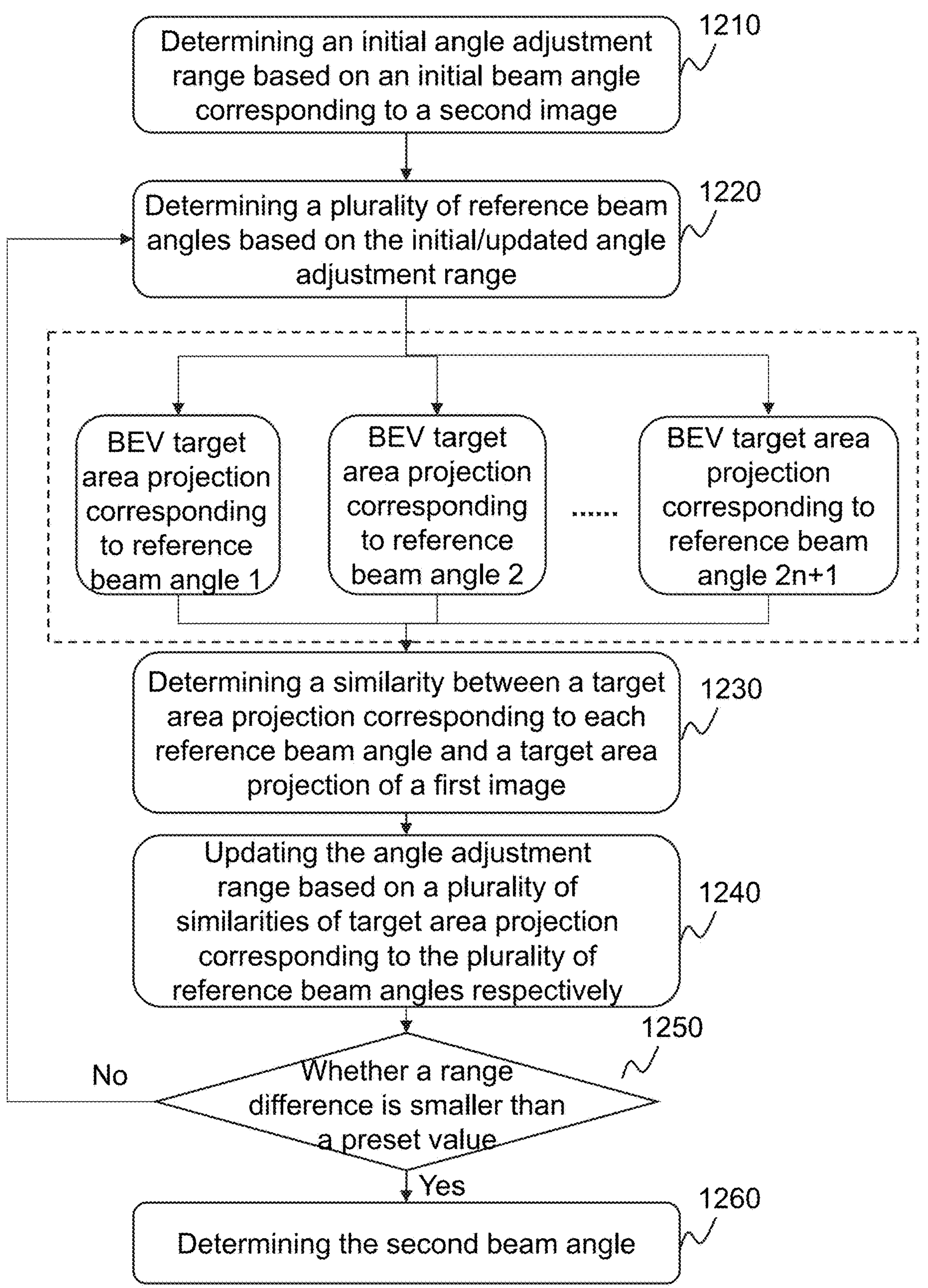
FIG. 12 is a flowchart illustrating an exemplary process for determining a second beam angle according to some embodiments of the present disclosure.

FIG. 12 is a flowchart illustrating an exemplary process for determining a second beam angle according to some embodiments of the present disclosure. In some embodiments, process 1200 may be executed by the medical system 100. For example, the process 1200 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 1200. The operations of the illustrated process presented below are intended to be illustrative. In some embodiments, the process 1200 may be accomplished with one or more additional operations not described and/or without one or more of the operations discussed. Additionally, the order of the operations of process 1200 illustrated in FIG. 12 and described below is not intended to be limiting.

In 1210, the processing device 130 (e.g., an adjusted radiation field information determination module, the processor 210) may determine an initial angle adjustment range based on an initial beam angle corresponding to a second image.

In some embodiments, the processing device 130 may determine the initial angle adjustment range based on the initial beam angle and a preset value. The preset value may be any integer value (e.g., 8°, 10°, 11°, 13°, 14°, 15°), which may be set according to an actual need. In some embodiments, the processing device 130 may determine the initial angle adjustment range based on a sum of the initial beam angle and the preset value and/or a difference between the initial beam angle and the preset value. For example, the initial angle adjustment range may be [A'−k, A'+k]. A' represents the initial beam angle and k represents the preset value.

In 1220, the processing device 130 (e.g., the adjusted radiation field information determination module, the processor 210) may determine a plurality of reference beam angles based on the initial/updated angle adjustment range.

In some embodiments, the processing device 130 may determine the plurality of reference beam angles based on the initial angle adjustment range. In some embodiments, the processing device 130 may determine an odd count of reference beam angles based on the initial angle adjustment range. For example, the processing device 130 may determine 2n+1 reference beam angles based on the initial angle adjustment range [A'−k, A'+k], which may be respectively expressed as $$A'-k,\ A'-\frac{n-1}{n}*k,\ \ldots\ ,\ A'-\frac{1}{n}*k,\ A',\ A'+\frac{1}{n}*k,\ \ldots\ ,\ A'+\frac{n-1}{n}*k,\ A'+k.$$

In some embodiments, the processing device 130 may determine any count of (e.g., 2n, 2n−1) reference beam angles based on the initial angle adjustment range, which is not limited in the present disclosure.

In some embodiments, the count of reference beam angles determined based on the initial angle adjustment range may be consistent with the count of reference beam angles determined based on the updated angle adjustment range.

In 1230, the processing device 130 (e.g., the adjusted radiation field information determination module, the processor 210) may determine a similarity between a target area projection (e.g., a BEV target area projection) corresponding to each reference beam angle and a target area projection (e.g., a BEV target area projection) of a first image.

In some embodiments, for each reference beam angle, the processing device 130 may obtain a target area projection of a second image in the BEV plane corresponding to the reference beam angle. For example, the processing device 130 may determine a BEV target area projection of the second image corresponding to the reference beam angle 1 (i.e., A'−k), a BEV target area projection of the second image corresponding to the reference beam angle 2

$$\left(\text{i.e., } A'-\frac{n-1}{n}*k\right),$$

. . . , a BEV target area projection of the second image corresponding to the reference beam angle 2n+1 (i.e., A'+k).

In 1240, the processing device 130 (e.g., the adjusted radiation field information determination module, the processor 210) may update the angle adjustment range based on a plurality of similarities of target area projection corresponding to the plurality of reference beam angles respectively.

In some embodiments, the processing device 130 may update the angle adjustment range based on the plurality of similarities of target area projection corresponding to the plurality of reference beam angles respectively. For example, the processing device 130 may determine a new angle adjustment range $$\left[A'+\frac{m}{n}*k,\ A'+\frac{m+2}{n}*k\right]$$

based on the plurality of similarities of target area projection $a_0, a_1, \ldots, a_{n-1}, a_n, a_{n+1}, \ldots, a_{2n-1}, a_{2n}$, wherein m may be any positive integer.

In some embodiments, the processing device 130 may determine the second beam angle based on the updated angle adjustment range. Specifically, in 1250, the processing device 130 (e.g., the adjusted radiation field information determination module, the processor 210) may determine whether a range difference of the angle adjustment range is smaller than a preset value.

In some embodiments, the processing device 130 may determine whether the range difference of the updated angle adjustment range is smaller than the preset value. If the range difference of the updated angle adjustment range is smaller than the preset value, the processing device 130 may determine the adjusted beam angle by executing operation 1260. If the range difference of the updated angle adjustment range is greater than or equal to the preset value, the processing device 130 may perform the beam angle adjustment process by executing operation 1220 again. For example, if the updated angle adjustment range is [15°, 17°] and the range difference 17°−15°=2° is greater than the preset value 1°, the processing device 130 may execute operations 1220-1240 again based on the range until the range difference of the angle adjustment range is smaller than the preset value 1°.

In some embodiments, the preset value may be any reasonable value (e.g., 0.5°, 1°), which is not limited in the present disclosure.

In 1260, the processing device 130 (e.g., the adjusted radiation field information determination module, the processor 210) may determine the second beam angle.

In some embodiments, the processing device 130 may determine the second beam angle based on the updated angle adjustment range. For example, the processing device 130 may determine an angle corresponding to a median in the angle adjustment range as the second beam angle. As another example, the processing device 130 may determine a maximum value or a minimum value in the angle adjustment range as the second beam angle. As yet another example, the processing device 130 may determine an average value of all angles in the angle adjustment range as the second beam angle.

In some embodiments, the processing device 130 may determine the updated angle adjustment range as a second beam angle range. For example, the processing device 130 may determine the angle adjustment range with the range difference smaller than the preset value as the second beam angle range, accordingly, the second beam angle corresponding to the treatment plan updated based on the second image may be any beam angle in the second beam angle range. In some embodiments, when the second image corresponds to a beam angle range (e.g., the adjusted beam angle range mentioned above), the processing device 130 may determine a second collimator angle and a second lock field parameter corresponding to at least one beam angle in the beam angle range. For example, the processing device 130 may determine a second collimator angle and a second lock field parameter corresponding to a beam angle 1 in the second beam angle range; then rotate to a beam angle 2 and determine a second collimator angle and a second lock field parameter corresponding to the beam angle 2; and repeat the process until traversing all beam angles in the second beam angle range. As another example, the processing device 130 may determine the second collimator angle and the second lock field parameter corresponding to any beam angle (e.g., the maximum beam angle and the median beam angle) in the second beam angle range.

According to the embodiments of the present disclosure, the initial beam angle corresponding to the second image may be determined based on the rigid registration parameter and the initial beam angle may be further adjusted based on the target area projection similarity, so that the radiation field corresponding to the second image may be close or substantially close to the radiation field determined by the first image, thereby ensuring the effect of radiotherapy.

It should be noted that the above description regarding the process 1200 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1200 may be accomplished with one or more additional operations not described and/or without one or more of the operations discussed above.

Figure 14:
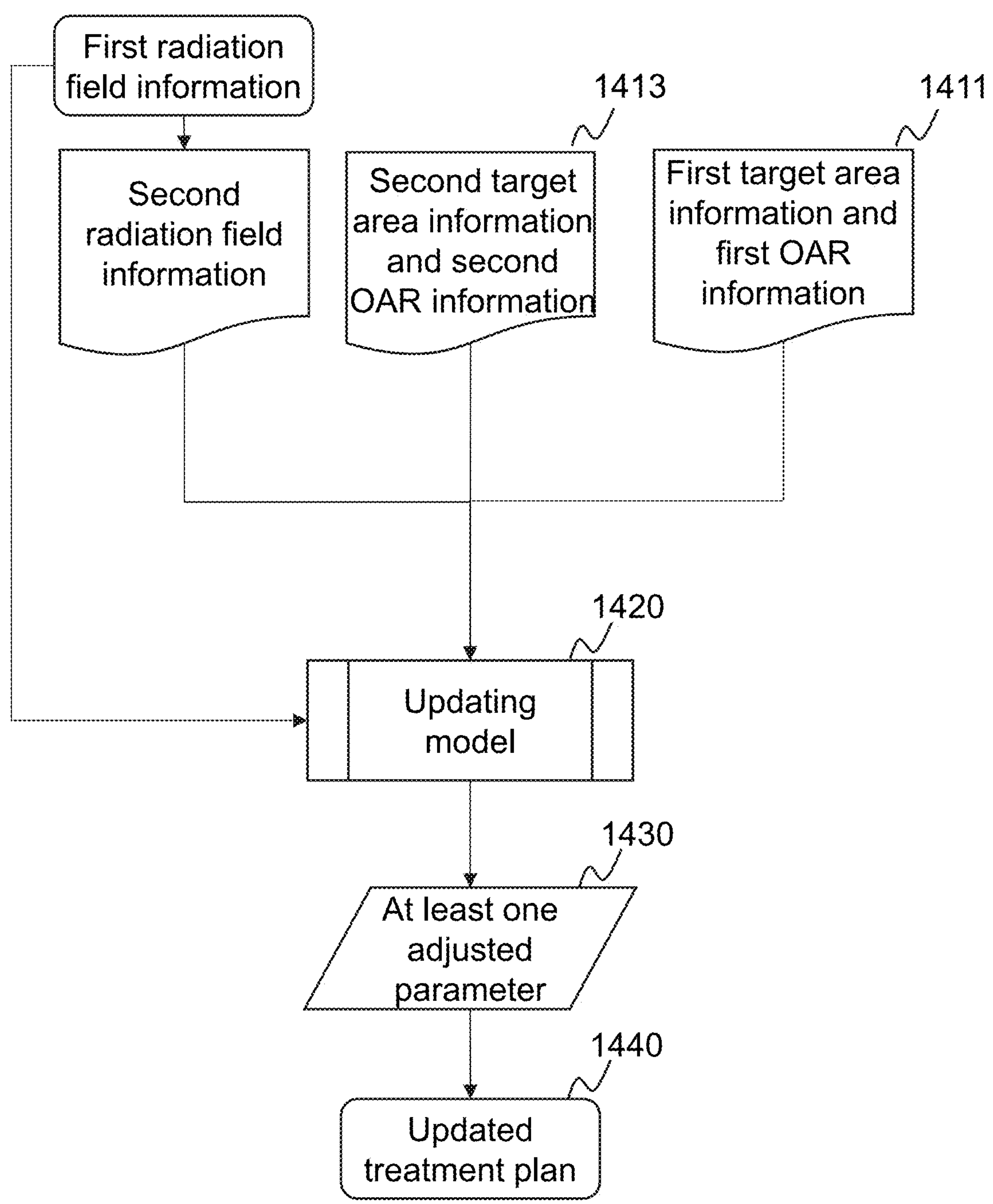
FIG. 14 is a flowchart illustrating an exemplary process for updating a treatment plan according to some embodiments of the present disclosure.

FIG. 14 is a flowchart illustrating an exemplary process for updating a treatment plan according to some embodiments of the present disclosure. In some embodiments, process 1400 may be executed by the medical system 100. For example, the process 1400 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 1400. The operations of the illustrated process presented below are intended to be illustrative. In some embodiments, the process 1400 may be accomplished with one or more additional operations not described and/or without one or more of the operations discussed. Additionally, the order of the operations of process 1400 illustrated in FIG. 14 and described below is not intended to be limiting.

In 1411, the processing device 130 (e.g., a treatment plan determination module, the processor 210) may obtain first target area information and first OAR information corresponding to a first image.

In some embodiments, the processing device 130 may obtain the first target area information and the first OAR information by analyzing the first image. For example, the processing device 130 may input the first image into a trained image recognition model. The image recognition model may output the corresponding first target area information and the first OAR information through analysis and processing. As another example, the processing device 130 may determine the first target area information and the first OAR information by counting pixel values in the first image.

In 1413, the processing device 130 (e.g., the treatment plan determination module, the processor 210) may obtain second target area information and second OAR information corresponding to a second image.

In some embodiments, the processing device 130 may determine the second target area information and the second OAR information by analyzing the second image. In some embodiments, the processing device 130 may determine the first target area information, the first OAR information, the second target area information, and the second OAR information in the same or different manners.

In 1420, the processing device 130 (e.g., the treatment plan determination module, the processor 210) may input first radiation field information, second radiation field information, the first target area information, the first OAR information, the second target area information, and the second OAR information into an updating model.

In some embodiments, the processing device 130 may input the first radiation field information corresponding to the first image, the second radiation field information corresponding to the second image, the first target area information, the first OAR information, the second target area information, and the second OAR information into the updating model.

In some embodiments, the processing device 130 may input the first image, the second image, the first radiation field information, and the second radiation field information into the updating model. In some embodiments, the processing device 130 may input the first radiation field information and the second radiation field information into the updating model. In some embodiments, the processing device 130 may input the first image and the second image into the updating model.

In 1430, the processing device 130 (e.g., the treatment plan determination module, the processor 210) may determine at least one adjusted parameter corresponding to at least one parameter of a treatment plan based on an output of the updating model.

In some embodiments, the updating model may analyze and process the input first radiation field information, the second radiation field information, the first target area information, the first OAR information, the second target area information, and the second OAR information and output at least one adjustment amount. The at least one adjustment amount may correspond to the at least one parameter of the treatment plan (which may be determined based on the first radiation field information). For example, the adjustment amount may include at least one of a beam angle adjustment amount, a collimator angle adjustment amount, a lock field parameter adjustment amount, or a radiation dose adjustment amount. Further, the processing device 130 may determine the at least one adjusted parameter based on the at least one adjustment amount corresponding to at least one parameter respectively. For example, the processing device 130 may adjust a radiation dose value of an initial treatment plan based on the radiation dose adjustment amount to obtain the updated treatment plan.

In some embodiments, the updating model may be trained based on a plurality of training samples. For example, the updating model may be determined by training a preliminary machine learning model based on a plurality of third training samples. In some embodiments, each third training sample may include sample first target area information, sample first OAR information, sample second target area information, sample second OAR information, the first radiation field information (e.g., target radiation field information), the second radiation field information, and a parameter adjustment amount. In some embodiments, the processing device 130 may use the sample first target area information, the sample first OAR information, the sample second target area information, the sample second OAR information, the first radiation field information (e.g., target radiation field information), and the second radiation field information of the plurality of third training samples as an input of the model training, use the parameter adjustment amount as a label, and train a third preliminary model to obtain a trained updating model. In some embodiments, the updating model may include a CNN model, a fully connected neural network model, and a RNN model.

In some embodiments, each third training sample may include a sample first image, a sample second image, the first radiation field information (e.g., target radiation field information), the second radiation field information, and a corresponding parameter adjustment amount. For example, the processing device 130 may use the sample first image, the sample second image, the first radiation field information (e.g., target radiation field information), and the second radiation field information of the plurality of third training samples as the input of the model training, use the parameter adjustment amount as the label, and train the third preliminary model to obtain the trained updating model.

In some embodiments, each third training sample may include the first radiation field information (e.g., target radiation field information), the second radiation field information, and the corresponding parameter adjustment amount. For example, the processing device 130 may use the first radiation field information, the second radiation field information of the plurality of third training samples as the input of the model training, use the parameter adjustment amount as the label, and train the third preliminary model to obtain the trained updating model.

In some embodiments, each third training sample may include the sample first image, the sample second image, and the corresponding parameter adjustment amount. For example, the processing device 130 may use the sample first image and the sample second image of the plurality of third training samples as the input of the model training, use the parameter adjustment amount as the label, and train the third preliminary model to obtain the trained updating model.

In 1440, the processing device 130 (e.g., the treatment plan determination module, the processor 210) may update the treatment plan based on the at least one adjusted parameter corresponding to the at least one parameter.

In some embodiments, the processing device 130 may replace the at least one parameter (original parameter(s)) of the treatment plan with the at least one adjusted parameter to update the treatment plan.

According to the embodiments of the present disclosure, the parameter adjustment amount of the treatment plan may be determined by using an updating model and the treatment plan of the object may be updated based on the adjustment amount, which can improve the updating efficiency and accuracy of the treatment plan.

It should be noted that the above description regarding the process 1400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1400 may be accomplished with one or more additional operations not described and/or without one or more of the operations discussed above.

Figure 15:
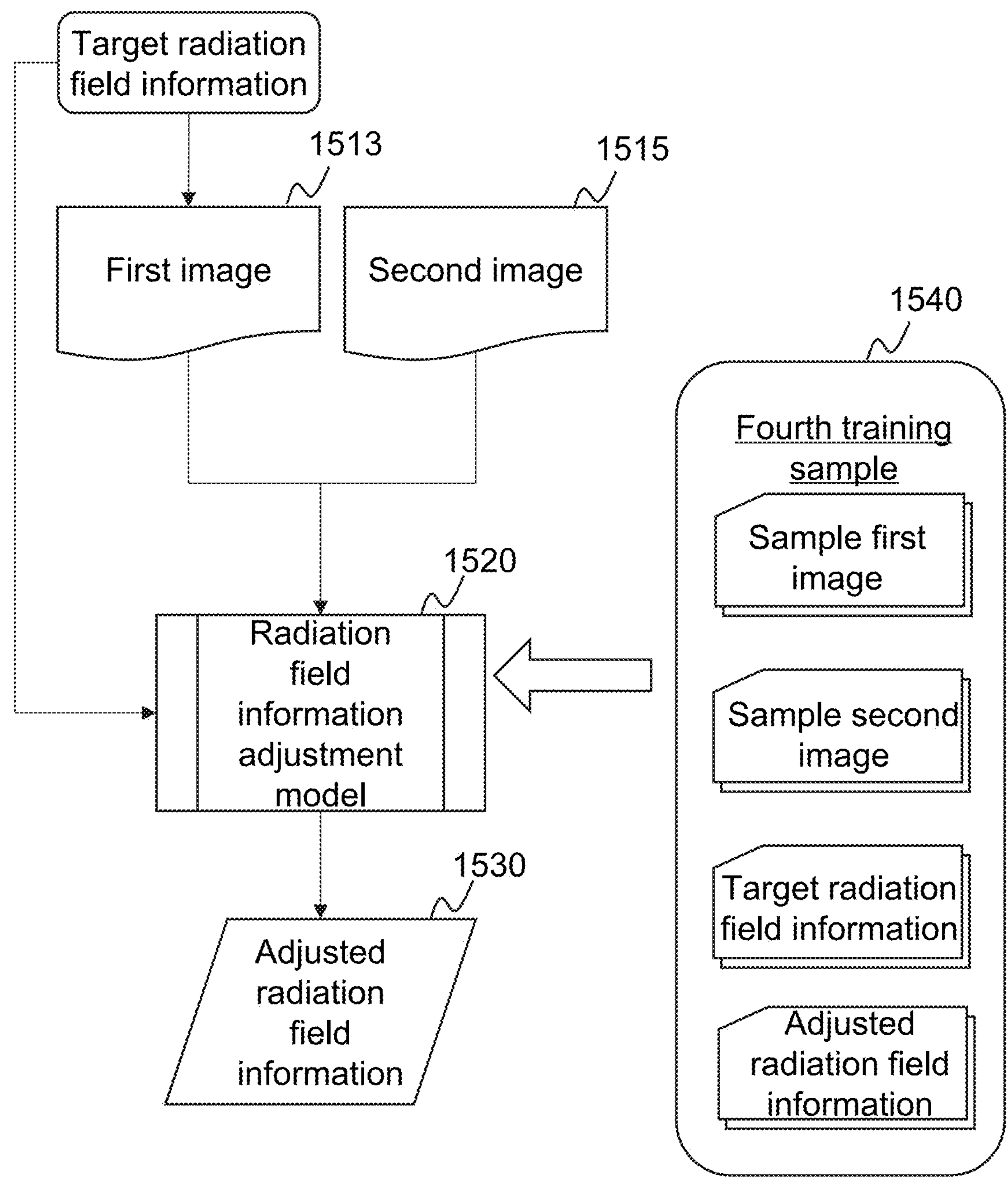
FIG. 15 is a flowchart illustrating an exemplary process for determining adjusted radiation field information according to other embodiments of the present disclosure.

FIG. 15 is a flowchart illustrating an exemplary process for determining adjusted radiation field information according to some embodiments of the present disclosure. In some embodiments, process 1500 may be executed by the medical system 100. For example, the process 1500 may be implemented as a set of instructions stored in the storage device (e.g., the storage device 150). In some embodiments, the processing device 130 (e.g., the processor 210 of the computing device 200 and/or one or more modules illustrated in FIG. 3) may execute the set of instructions and may accordingly be directed to perform the process 1500. The operations of the illustrated process presented below are intended to be illustrative. In some embodiments, the process 1500 may be accomplished with one or more additional operations not described and/or without one or more of the operations discussed. Additionally, the order of the operations of process 1500 illustrated in FIG. 15 and described below is not intended to be limiting.

In 1513, the processing device 130 (e.g., a treatment plan determination module, the processor 210) may obtain a first image of an object corresponding to target radiation field information.

In some embodiments, the first image may be collected at the same time as the target radiation field information is determined, or after the target radiation field information is determined. For example, the processing device 130 may obtain a first image of an object of a same size and direction or a similar size and direction corresponding to the target field information. As another example, as described in connection with the above, the target field information may be determined when the patient is diagnosed with a lesion, and correspondingly, the first image may be a medical image collected when the patient is diagnosed with the lesion. More descriptions may be found in the operation 1010 and the descriptions thereof.

In 1515, the processing device 130 (e.g., the treatment plan determination module, the processor 210) may obtain a second image of the object. More descriptions may be found in the operation 1020 and the descriptions thereof.

In 1520, the processing device 130 (e.g., the treatment plan determination module, the processor 210) may input the target radiation field information, the first image, and the second image into a radiation field information adjustment model.

In some embodiments, the processing device 130 may use the second image of the object, the target radiation field information, and the first image corresponding to the target radiation field information as an input of the radiation field information adjustment model, so as to determine the adjusted radiation field information (e.g., second radiation field information) corresponding to the second image. Combine with FIG. 10, the adjusted radiation field information may include an adjusted beam angle (e.g., second beam angle), an adjusted collimator angle (e.g., second collimator angle), and an adjusted lock field parameter (e.g., second lock field parameter). In some implementations, the radiation field information adjustment model may simultaneously output the adjusted beam angle, the adjusted collimator angle, and the adjusted lock field parameter corresponding to the second image. More descriptions may be found in FIG. 10 and/or FIG. 11 and the descriptions thereof.

In 1530, the processing device 130 (e.g., the treatment plan determination module, the processor 210) may determine the adjusted radiation field information corresponding to the second image.

In some embodiments, the radiation field information adjustment model may analyze the target radiation field information, the first image, and the second image and output the adjusted radiation field information (e.g., second radiation field information). In some embodiments, the processing device 130 may determine the output adjusted radiation field information as the adjusted radiation field information corresponding to the second image.

In some embodiments, the radiation field information adjustment model (e.g., a CNN model, a fully connected neural network model, a RNN model) may be trained based on a plurality of training samples. As illustrated in 1540, the radiation field information adjustment model may be determined by training a preliminary machine learning model based on a plurality of fourth training samples.

In some embodiments, each fourth training sample may include a sample first image, a sample second image, the target radiation field information, and the adjusted radiation field information (e.g., second radiation field information). In some embodiments, the plurality of fourth training samples may include a plurality of types. For example, the processing device 130 may obtain historical radiation therapy data (e.g., a historical treatment plan) of various types of sample cases such as a breast tumor, a lung tumor, an uterine tumor, a gastric tumor, an epithelial tumor, a mesenchymal tumor, a neurogenic tumor, a lymphogenic tumor, etc., and accordingly determine the plurality of fourth training samples. In some embodiments, the processing device 130 may obtain the sample first image, the sample second image, the target radiation field information, and the adjusted radiation field information corresponding to a plurality of cases of a same part (e.g., a breast, a thyroid) as the fourth training sample.

In some embodiments, the processing device 130 may use the sample first image, the sample second image, and the target radiation field information of the plurality of fourth training samples as an input of the model training, use the adjusted radiation field information (e.g., second radiation field information) as a label, and train a fourth preliminary model to obtain a trained field information adjustment model.

The adjusted radiation field information may be determined using the machine learning model, which can improve the efficiency and accuracy of radiation field parameter formulation and help realize automatic field deployment at the same time. The radiation field parameter formulation may be integrated into the online automatic planning process, which is conducive to the realization of a one-stop workflow.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A system for determining radiation field information, comprising:
- at least one storage medium including a set of instructions; and
- at least one processor in communication with the at least one storage medium, wherein when executing the set of instructions, the at least one processor is directed to cause the system to perform operations including:
  - obtaining a candidate beam angle range for an object, wherein the candidate beam angle range is determined by the at least one processor for the object based on information of the object, or determined based on user input information;
  - for at least one candidate beam angle of the candidate beam angle range, determining at least one candidate lock field parameter corresponding to the candidate beam angle based on a region of interest projection and/or a radiation field projection; and
  - determining target radiation field information based on the at least one candidate lock field parameter.

2. The system of claim 1, wherein the information of the object includes case information of the object, and the obtaining the candidate beam angle range includes:
- determining, based on the case information of the object, a target historical case corresponding to the case information, the case information including a tumor type or reference information related to a region of interest (ROI); and
- determining the candidate beam angle range for the object based on the target historical case; or
- the obtaining the candidate beam angle range includes:
- adjusting the candidate beam angle range of the object based on an adjustment parameter related to the candidate beam angle range input by a user through a terminal device, wherein the adjustment parameter includes at least one of a maximum interval, a minimum interval, an angle interval, and a count of angles.

3. The system of claim 1, wherein the determining at least one candidate lock field parameter corresponding to the candidate beam angle based on a region of interest projection and/or a radiation field projection, includes:
- determining the at least one candidate lock field parameter corresponding to the candidate beam angle using a lock field parameter determination model based on the region of interest projection and/or the radiation field projection.

4. The system of claim 1, wherein the determining at least one candidate lock field parameter corresponding to the candidate beam angle based on a region of interest projection and/or a radiation field projection includes:
- determining the at least one candidate lock field parameter corresponding to the candidate beam angle using a radiation field information determination model based on the region of interest projection and/or the radiation field projection.

5. The system of claim 1, wherein the determining target radiation field information based on the at least one candidate lock field parameter includes:
- for each of the at least one candidate beam angle, determining a candidate radiation field corresponding to the candidate beam angle based on the at least one candidate lock field parameter corresponding to the candidate beam angle; and
- determining the target radiation field information using a fluence map optimization-based multi-stage optimization approach based on the at least one candidate radiation field corresponding to the at least one candidate beam angle.

6. The system of claim 1, wherein the operations further include:
- obtaining a first image of the object corresponding to the target radiation field information;
- obtaining a second image of the object;
- determining relevant information of the second image and the first image; and
- determining adjusted radiation field information corresponding to the second image based on the relevant information and the target radiation field information.

7. The system of claim 6, wherein the first image or the second image includes at least one of target area information or organ at risk (OAR) information of the object.

8. The system of claim 6, wherein
the relevant information includes at least one of a registration parameter or a target area projection similarity; and
the registration parameter includes a rigid registration parameter or a non-rigid registration parameter determined based on anatomical structures in the first image and the second image.

9. The system of claim 6, wherein the determining adjusted radiation field information corresponding to the second image based on the relevant information and the target radiation field information includes:
determining an initial beam angle corresponding to the second image based on a rigid registration parameter of the second image and the first image and a target beam angle of the target radiation field information; and
determining an adjusted beam angle corresponding to the second image by adjusting the initial beam angle based on a target area projection similarity of the second image and the first image.

10. The system of claim 9, wherein the determining an adjusted beam angle corresponding to the second image by adjusting the initial beam angle based on a target area projection similarity of the second image and the first image includes:
determining an initial angle adjustment range based on the initial beam angle corresponding to the second image;
determining a plurality of reference beam angles based on the initial angle adjustment range;
determining a similarity between a target area projection corresponding to each reference beam angle and a target area projection of the first image;
updating the initial angle adjustment range based on a plurality of similarities of target area projection corresponding to the plurality of reference beam angles respectively; and
determining the adjusted beam angle based on the updated angle adjustment range.

11. The system of claim 6, wherein the determining adjusted radiation field information corresponding to the second image based on the relevant information and the target radiation field information includes:
determining an adjusted collimator angle corresponding to the second image based on a rigid registration parameter of the second image and the first image and a target collimator angle of the target radiation field information.

12. The system of claim 6, wherein the determining adjusted radiation field information corresponding to the second image based on the relevant information and the target radiation field information includes:
determining an adjusted lock field parameter corresponding to the second image based on a non-rigid registration parameter of the second image and the first image and a target lock field parameter of the target radiation field information.

13. The system of claim 6, wherein after obtaining the second image of the object, the operations further include:
determining a similarity between the second image and the first image; and
providing a notification in response to a determination that the similarity is smaller than a preset threshold.

14. The system of claim 6, wherein the operations further include:
updating a treatment plan of the object based on the adjusted radiation field information, wherein the treatment plan is determined based on the target radiation field information.

15. The system of claim 14, wherein the updating a treatment plan of the object based on the adjusted radiation field information includes:
obtaining first target area information and first OAR information corresponding to the first image;
obtaining second target area information and second OAR information corresponding to the second image;
determining at least one adjusted parameter corresponding to at least one parameter of the treatment plan using an updating model based on the target radiation field information, the adjusted radiation field information, the first target area information, the first OAR information, the second target area information, and the second OAR information; and
updating the treatment plan of the object based on the at least one adjusted parameter corresponding to the at least one parameter.

16. The system of claim 1, wherein the operations further include:
obtaining a first image of the object corresponding to the target radiation field information;
obtaining a second image of the object; and
determining, based on the first image and the second image, adjusted target radiation field information corresponding to the second image using a radiation field information adjustment model.

17. A method for determining radiation field information, comprising:
obtaining a candidate beam angle range for an object; wherein the candidate beam angle range includes a candidate beam angle range determined by at least one processing device for the object based on information of the object, or determined based on user input information;
for at least one candidate beam angle of the candidate beam angle range, determining at least one candidate lock field parameter corresponding to the candidate beam angle based on a region of interest projection and/or a radiation field projection; and
determining target radiation field information based on the at least one candidate lock field parameter.

18. The method of claim 17, wherein the determining target radiation field information based on the at least one candidate lock field parameter includes:
for each of the at least one candidate beam angle, determining a candidate radiation field corresponding to the candidate beam angle based on the at least one candidate lock field parameter corresponding to the candidate beam angle; and
determining the target radiation field information using a fluence map optimization-based multi-stage optimization approach based on the at least one candidate radiation field corresponding to the at least one candidate beam angle.

19. The method of claim 17, further comprising:
obtaining a first image of the object corresponding to the target radiation field information;
obtaining a second image of the object;
determining relevant information of the second image and the first image; and determining adjusted target radiation field information corresponding to the second image based on the relevant information and the target radiation field information.

20. A non-transitory computer readable medium storing instructions, the instructions, when executed by at least one processor, causing the at least one processor to implement a method for determining radiation field information comprising:

obtaining a candidate beam angle range for an object; wherein the candidate beam angle range includes a candidate beam angle range determined by at least one processing device for the object based on information of the object, or determined based on user input information;

for at least one candidate beam angle of the candidate beam angle range, determining at least one candidate lock field parameter corresponding to the candidate beam angle based on a region of interest projection and/or a radiation field projection; and determining target radiation field information based on the at least one candidate lock field parameter.

* * * * *